(12) United States Patent
Kapur et al.

(10) Patent No.: US 12,076,363 B2
(45) Date of Patent: Sep. 3, 2024

(54) PEPTIDE EPOXYKETONE PROTEASOME INHIBITORS IN COMBINATION WITH PIM KINASE INHIBITORS FOR TREATMENT OF CANCERS

(71) Applicant: ONYX PHARMACEUTICALS, INC., Thousand Oaks, CA (US)

(72) Inventors: Shirin Kapur, Burlingame, CA (US); Alana Lerner, San Francisco, CA (US); Christopher J. Kirk, San Francisco, CA (US); Eric Lowe, Moraga Town, CA (US); Tracey Lin, Union City, CA (US)

(73) Assignee: ONYX PHARMACEUTICALS, INC., Thousand Oaks, CA (US)

( * ) Notice: Subject to any disclaimer, the term of this patent is extended or adjusted under 35 U.S.C. 154(b) by 0 days.

(21) Appl. No.: 17/482,699

(22) Filed: Sep. 23, 2021

(65) Prior Publication Data

US 2022/0265758 A1 Aug. 25, 2022

Related U.S. Application Data

(63) Continuation of application No. 17/150,319, filed on Jan. 15, 2021, now abandoned, which is a continuation of application No. 16/895,328, filed on Jun. 8, 2020, now abandoned, which is a continuation of application No. 16/659,123, filed on Oct. 21, 2019, now abandoned, which is a continuation of application No. 16/289,255, filed on Feb. 28, 2019, now abandoned, which is a continuation of application No. 14/905,179, filed as application No. PCT/US2014/046950 on Jul. 17, 2014, now abandoned.

(60) Provisional application No. 61/863,760, filed on Aug. 8, 2013, provisional application No. 61/863,768, filed on Aug. 8, 2013, provisional application No. 61/856,636, filed on Jul. 19, 2013, provisional application No. 61/856,626, filed on Jul. 19, 2013.

(51) Int. Cl.
| | | |
|---|---|---|
| *A61K 38/07* | (2006.01) |
| *A61K 31/426* | (2006.01) |
| *A61K 31/427* | (2006.01) |
| *A61K 31/454* | (2006.01) |
| *A61K 31/4545* | (2006.01) |
| *A61K 31/4745* | (2006.01) |
| *A61K 31/5025* | (2006.01) |
| *A61K 31/506* | (2006.01) |
| *A61K 31/5377* | (2006.01) |
| *A61K 38/04* | (2006.01) |
| *A61K 38/06* | (2006.01) |
| *A61K 38/08* | (2019.01) |
| *A61K 45/06* | (2006.01) |
| *C07K 5/083* | (2006.01) |
| *C07K 5/107* | (2006.01) |

(52) U.S. Cl.
CPC ............ *A61K 38/07* (2013.01); *A61K 31/426* (2013.01); *A61K 31/427* (2013.01); *A61K 31/454* (2013.01); *A61K 31/4545* (2013.01); *A61K 31/4745* (2013.01); *A61K 31/5025* (2013.01); *A61K 31/506* (2013.01); *A61K 31/5377* (2013.01); *A61K 38/04* (2013.01); *A61K 38/06* (2013.01); *A61K 38/08* (2013.01); *A61K 45/06* (2013.01); *C07K 5/081* (2013.01); *C07K 5/1016* (2013.01)

(58) Field of Classification Search
None
See application file for complete search history.

(56) References Cited

PUBLICATIONS

FDA "Carfilzomib" //wayback.archiveit.org/7993/*/http://www.fda.gov/Drugs/InformationOnDrugs/ApprovedDrugs/ucm312945.htm (Year: 2016).*

Keeton et al. "AZD1208, a Potent and Selective Pan-Pim Kinase Inhibitor, Demonstrates Efficacy in Preclinical Models of Acute Myeloid Leukemia" Blood doi:10.1182/blood-2013-04-495366. (Year: 2013).*

Meja et al. "PIM and ATK kinase inhibitors show synergistic cytotoxicity in acute myeloid leukaemia that is associated with convergence on mTOR and MCL1 pathways" Brit. J. Haem. 167:69-79. (Year: 2014).*

Cervantes-Gomez et al. "Biological Effects of the Pim Kinase Inhibitor, SGI-1776, in Multiple Myeloma" Clin. Lymphoma Myeloma Leuk. 13:S317-S329. (Year: 2013).*

Mimura et al. "Selective and potent Akt inhibition triggers anti-myeloma activities and enhances fatal endoplasmic reticulum stress induced by proteasome inhibition" Cancer Res. 74:4458-4469. (Year: 2014).*

* cited by examiner

*Primary Examiner* — Melissa L Fisher
*Assistant Examiner* — Zachary J Miknis
(74) *Attorney, Agent, or Firm* — MARSHALL, GERSTEIN & BORUN LLP

(57) ABSTRACT

This disclosure provides methods of treating a cancer in a patient using a peptide epoxyketone proteasome inhibitor in combination with a PIM kinase inhibitor.

16 Claims, 4 Drawing Sheets

PEPTIDE EPOXYKETONE PROTEASOME INHIBITORS IN COMBINATION WITH PIM KINASE INHIBITORS FOR TREATMENT OF CANCERS

CROSS REFERENCE TO RELATED APPLICATIONS

The benefit of each of U.S. Provisional Application Nos. 61/856,636, filed Jul. 19, 2013; 61/863,768, filed Aug. 8, 2013; 61/856,626, filed Jul. 19, 2013, and 61/863,760, filed Aug. 8, 2013, is claimed, the disclosures of which are each incorporated by reference in their entirety.

TECHNICAL FIELD

This disclosure relates to the treatment of a cancer in a patient through administration of peptide epoxyketone proteasome inhibitors in combination with PIM kinase inhibitors.

BACKGROUND

The proteasome has been validated as a therapeutic target, as demonstrated by the United States Food & Drug Administration approval of bortezomib, a boronic acid proteasome inhibitor, for the treatment of various cancer indications, including multiple myeloma. However, other more highly proteasome-specific inhibitors that could have fewer toxic side effects have recently been described. These compounds include peptide epoxyketones such as epoxomicin, described in U.S. Pat. No. 6,831,099, the contents of which are hereby incorporated by reference, and those peptide epoxyketone proteasome compounds, compositions, and polymorphs described in U.S. Pat. Nos. 7,687,456; 7,737, 112; 7,232,818; 7,417,042; 7,687,456; 8,207,125; 8,207, 126; 8,207,297; 8,324,174; and 8,367,617, the contents of each is hereby incorporated by reference in its entirety. For example, carfilzomib, a peptide epoxyketone proteasome inhibitor, was approved by the United States Food & Drug Administration for the treatment of relapsed and refractory multiple myeloma in 2012.

SUMMARY

Provided herein are methods for the treatment of a cancer in a patient, the method comprising administering to the patient a therapeutically effective amount of a compound of formula (I):

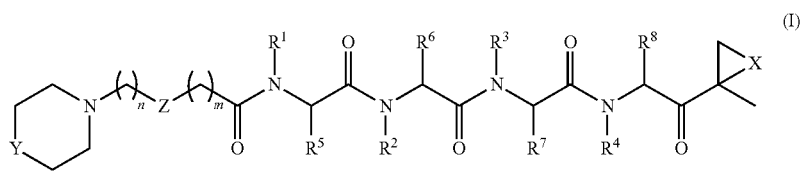

or a pharmaceutically acceptable salt thereof, wherein X is O, NH, or N-alkyl; Y is NH, N-alkyl, O, or $C(R^9)_2$; Z is O or $C(R^9)_2$; $R^1$, $R^2$, $R^3$, and $R^4$ are all hydrogen; each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether; $R^{10}$ and $R^{11}$ are independently selected from hydrogen and $C_{1-6}$alkyl, or $R^{10}$ and $R^{11}$ together form a 3- to 6-membered carbocyclic or heterocyclic ring; $R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; m is an integer from 0 to 2; n is an integer from 0 to 2, preferably 0 or 1; and a therapeutically effective amount of a PIM kinase inhibitor, or a pharmaceutically acceptable salt thereof. In some embodiments, X is O. In some embodiments, $R^5$, $R^6$, $R^7$, and $R^8$ are independently selected from $C_{1-6}$alkyl, $C_{1-6}$hydroxyalkyl, and $C_{1-6}$aralkyl; and $R^9$ is hydrogen. In some embodiments, $R^5$ and $R^7$ are independently $C_{1-6}$aralkyl and $R^6$ and $R^8$ are independently $C_{1-6}$alkyl. In some embodiments, Y is selected from N-alkyl, O, and $CH_2$. In some embodiments, Z is $CH_2$, and m and n are both 0. In some embodiments, Z is $CH_2$, m is 0, and n is 2. In some embodiments, Z is O, m is 1, and n is 2.

Also provided herein are methods using a compound of formula (I) having a structure of formula (II) or a pharmaceutically acceptable salt thereof:

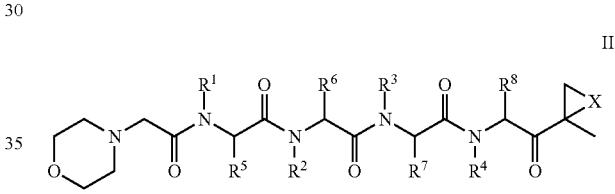

wherein X is selected from O, NH, and N-alkyl; $R^1$, $R^2$, $R^3$, and $R^4$ are all hydrogen; $R^5$, $R^6$, $R^7$, and $R^8$ are independently selected from hydrogen, $C_{1-6}$alkyl, $C_{1-6}$ hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether. In some embodiments, $R^5$, $R^6$, $R^7$, and $R^8$ are independently selected from $C_{1-6}$alkyl, $C_{1-6}$ hydroxyalkyl, and $C_{1-6}$aralkyl. In some embodiments, $R^5$ and $R^7$ are independently $C_{1-6}$aralkyl and $R^6$ and $R^8$ are independently $C_{1-6}$alkyl.

Also provided herein are methods using a compound of formula (I) having a structure of formula (III) or a pharmaceutically acceptable salt thereof,

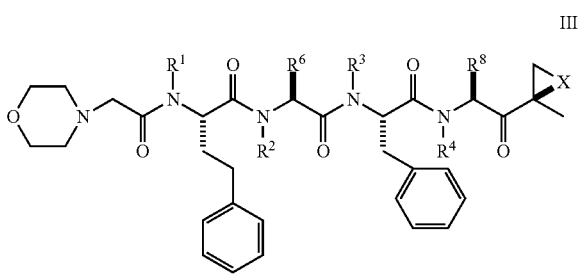

wherein X is O, NH, or N-alkyl; $R^1$, $R^2$, $R^3$, and $R^4$ are all hydrogen; $R^6$ and $R^8$ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether. In some embodiments, $R^6$ and $R^8$ are independently selected from $C_{1-6}$alkyl, $C_{1-6}$hydroxyalkyl, and $C_{1-6}$aralkyl. In some embodiments, $R^6$ and $R^8$ are independently $C_{1-6}$alkyl. For example, $R^6$ and $R^8$ can be both isobutyl.

In some embodiments, the methods using a compound of formula (I) has the structure:

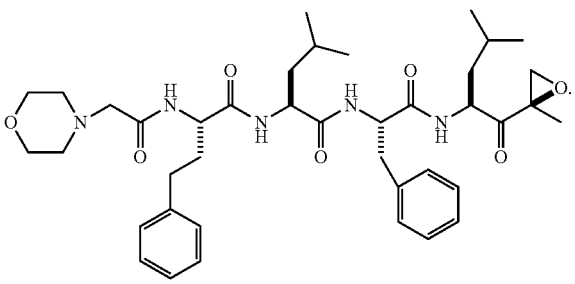 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Also provided herein are methods for the treatment of a cancer in a patient, the method comprising administering to the patient a therapeutically effective amount of a compound of formula (IV) or a pharmaceutically acceptable salt thereof:

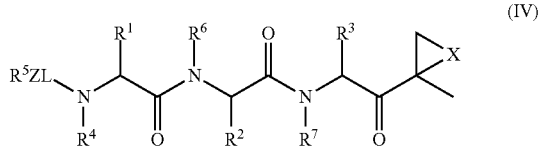

wherein L is selected from C=O, C=S, and $SO_2$; X is selected from O, S, NH, and N—$C_{1-6}$alkyl; Z is absent, $C_{1-6}$alkyl, or $C_{1-6}$alkoxy; $R^1$, $R^2$, and $R^3$ are each independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclylalkyl; $R^4$ is selected from hydrogen, $C_{1-6}$aralkyl, and $C_{1-6}$alkyl; $R^5$ is heteroaryl; and $R^6$ and $R^7$ are independently selected from hydrogen, $C_{1-6}$alkyl, and $C_{1-6}$aralkyl, and a therapeutically effective amount of a PIM kinase inhibitor, or a pharmaceutically acceptable salt thereof. In some embodiments, Z is absent. In some embodiments, $R^4$, $R^6$, and $R^7$ are independently selected from hydrogen and methyl. In some embodiments, L is C=O. In some embodiments, L is $SO_2$. In some embodiments, $R^1$, $R^2$, and $R^3$ are independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, $C_{1-6}$aralkyl, $C_{1-6}$heterocycloalkyl, $C_{1-6}$heteroaralkyl, and $C_{1-6}$carbocyclylalkyl. In some embodiments, any of $R^1$, $R^2$, and $R^3$ are independently $C_{1-6}$alkyl. In some embodiments, any of $R^1$, $R^2$, and $R^3$ are independently selected from methyl, ethyl, propyl, isopropyl, butyl, sec-butyl, and isobutyl. In some embodiments, any of $R^1$, $R^2$, and $R^3$ are independently propargyl. In some embodiments, any of $R^1$, $R^2$, and $R^3$ are independently $C_{1-6}$hydroxyalkyl. In some embodiments, any of $R^1$, $R^2$, and $R^3$ are independently selected from hydroxymethyl and hydroxyethyl. In some embodiments, any of $R^1$, $R^2$, and $R^3$ are independently $C_{1-6}$alkoxyalkyl. In some cases, any of $R^1$, $R^2$, and $R^3$ are independently selected from methoxymethyl and methoxyethyl. In some embodiments, any of $R^1$, $R^2$, and $R^3$ are independently $C_{1-6}$heteroaralkyl. In some embodiments, any of $R^1$, $R^2$, and $R^3$ are independently selected from imidazolylmethyl, pyrazolylmethyl, and thiazolylmethyl, and pyridylmethyl. In some embodiments, any of $R^1$, $R^2$, and $R^3$ are independently cyclohexylmethyl. In some embodiments, $R^1$, $R^2$, and $R^3$ are all different. In some embodiments, $R^1$ and $R^2$ are independently selected from $C_{1-6}$hydroxyalkyl and $C_{1-6}$alkoxyalkyl. In some embodiments, at least one of $R^1$ and $R^2$ is $C_{1-6}$alkoxyalkyl. In some embodiments, at least one of $R^1$ and $R^2$ is selected from methoxymethyl and methoxyethyl. In some embodiments, $R^3$ is selected from $C_{1-6}$alkyl and $C_{1-6}$aralkyl. In some embodiments, $R^3$ is $C_{1-6}$alkyl. In some embodiments, $R^3$ is selected from methyl, ethyl, isopropyl, sec-butyl, and isobutyl. For example, $R^3$ can be isobutyl. In some embodiments, $R^3$ is $C_{1-6}$aralkyl. For example, $R^3$ can be phenylmethyl. In some embodiments, $R^5$ is 5- or 6-membered heteroaryl. In some embodiments, $R^5$ is selected from isoxazole, isothiazole, furan, thiophene, oxazole, thiazole, pyrazole, or imidazole. In some embodiments, $R^5$ is selected from isoxazole, furan, or thiophene. In some embodiments, $R^5$ is furan or thiophene. In some embodiments, $R^5$ is unsubstituted furan-3-yl or thien-2-yl. In some embodiments, $R^5$ is isoxazol-3-yl or isoxazol-5-yl. In some embodiments, $R^5$ is isoxazol-3-yl that has a substituent at the 5-position. In some embodiments, $R^5$ is isoxazol-5-yl that has a substituent at the 3-position. In some embodiments, the substituent is selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, ($C_{1-6}$alkyl)$_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl. In some embodiments, the substituent is selected from methyl, ethyl, isopropyl, and cyclopropylmethyl. In some embodiments, the substituent is selected from $C_{1-6}$heteroaralkyl and $C_{1-6}$heterocycloalkyl. For instance, the substituent can be 1,2,4-triazol-5-ylmethyl. In certain embodiments, the substituent is azetidin-1-ylmethyl. In some embodiments, the substituent is

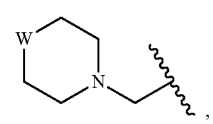

wherein W is O, NR, or $CH_2$, and R is H or $C_{1-6}$alkyl. In some embodiments, W is O. In some embodiments, the substituent is selected from $C_{1-6}$alkoxy and $C_{1-6}$alkoxyalkyl. In some embodiments, the substituent is selected from methoxy, ethoxy, methoxymethyl, and methoxyethyl. In some embodiments, the substituent is selected from carboxylic acid, aminocarboxylate, $C_{1-6}$alkylaminocarboxylate, $(C_{1-6}$alkyl$)_2$aminocarboxylate, or $C_{1-6}$alkylcarboxylate. For example, the substituent can be methyl carboxylate.

In some embodiments, the methods using a compound of formula (IV) has the structure:

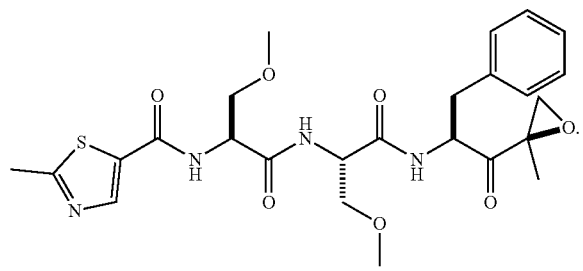 [SMILES: COC[C@H](NC(=O)c1cnc(C)s1)C(=O)N[C@@H](COC)C(=O)N[C@@H](Cc1ccccc1)C(=O)[C@@]1(C)CO1]

In some embodiments, the PIM kinase inhibitor is orally bioavailable. In some embodiments, the PIM kinase inhibitor is selective for one or more kinases selected from the group consisting of: PIM-1, PIM-2, and PIM-3. In some embodiments, the PIM kinase inhibitor is selective for PIM-2. In some embodiments, the PIM kinase inhibitor is selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof. In some embodiments, the PIM kinase inhibitor is (Z)-5-(4-propoxybenzylidene)thiazolidine-2,4-dione, or a pharmaceutically acceptable salt thereof. In some embodiments, the PIM kinase inhibitor is a dual PIM-1/PIM-2 inhibitor. In various cases, the PIM kinase inhibitor is a pan-PIM inhibitor (e.g., inhibitors the activity of each of PIM-1, PIM-2, and PIM-3). One example of a contemplated pan-PIM inhibitor is 5-[[2-[(3R)-3-aminopiperidin-1-yl]biphenyl-3-yl]methylidene]-1,3-thiazolidine-2,4-dione (also known as AZD1208).

In some embodiments, the cancer is refractory. In some embodiments, the cancer is resistant. In some embodiments, the cancer is one selected from the group consisting of: bone cancer, gynecological cancer, breast cancer, hematological malignancy, skin cancer, liver cancer, kidney cancer, pancreatic cancer, brain cancer, lung cancer, and prostate cancer. For example, the cancer can be a hematological malignancy.

In some embodiments, the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

In some embodiments, the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms. In some embodiments, the hematological malignancy is selected from the group consisting of: B-cell lymphoma and multiple myeloma. For example, the hematological malignancy can be multiple myeloma.

In some embodiments, the patient is one in whom PIM-2 kinase is overexpressed.

In some embodiments, the administration of the compound of formula (I) or formula (IV) and the PIM kinase inhibitor is performed concurrently. In some embodiments, the administration of the compound of formula (I) or formula (IV) and the PIM kinase inhibitor is performed sequentially. In some embodiments, the administration of the compound of formula (I) or formula (IV) is performed before administration of the PIM kinase inhibitor. In some embodiments, the administration of the compound of formula (I) or formula (IV) is performed after administration of the PIM kinase inhibitor.

Also provided herein is a method for the treatment of a hematological malignancy in a patient, the method comprising administering to the patient a therapeutically effective amount of a compound with the following formula:

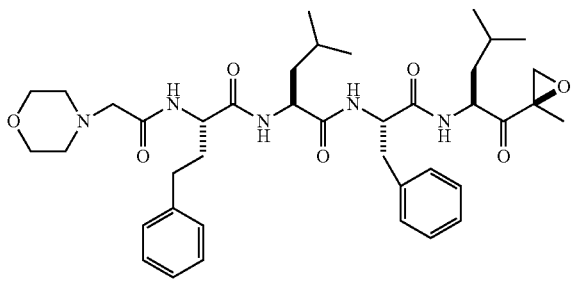 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of PIM kinase inhibitor, or a pharmaceutically acceptable salt thereof.

Additionally, provided herein is a method for the treatment of a hematological malignancy in a patient, the method comprising administering to the patient a therapeutically effective amount of a compound with the following formula:

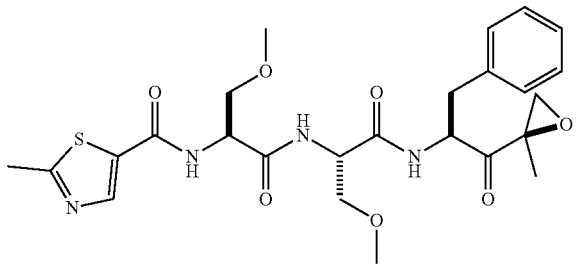 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM kinase inhibitor, or a pharmaceutically acceptable salt thereof.

Also provided herein is a method for the treatment of a hematological malignancy in a patient, the method comprising administering to the patient a therapeutically effective amount of a compound with the following formula:

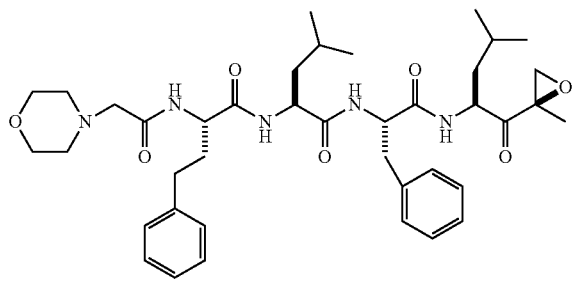 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of PIM-2 selective kinase inhibitor, or a pharmaceutically acceptable salt thereof.

Additionally, provided herein is a method for the treatment of a hematological malignancy in a patient, the method comprising administering to the patient a therapeutically effective amount of a compound with the following formula:

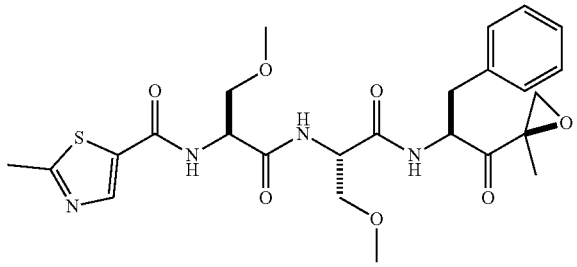 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM-2 selective kinase inhibitor, or a pharmaceutically acceptable salt thereof.

Also provided herein is a method for the treatment of a hematological malignancy in a patient, the method comprising administering to the patient a therapeutically effective amount of a compound with the following formula:

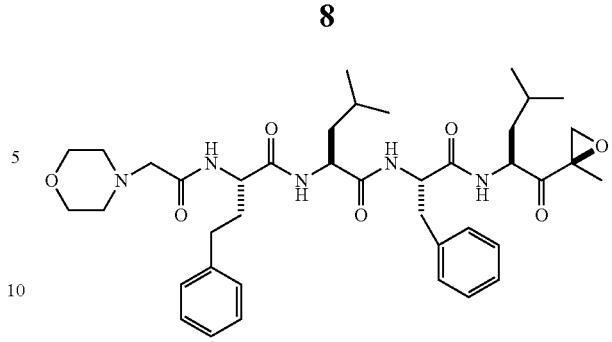

or a pharmaceutically acceptable salt thereof, and a therapeutically effective amount of PIM kinase inhibitor selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

Also provided herein is a method for the treatment of a hematological malignancy in a patient, the method comprising administering to the patient a therapeutically effective amount of a compound with the following formula:

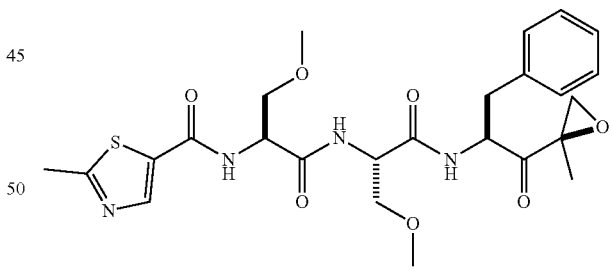

or a pharmaceutically acceptable salt thereof, and a therapeutically effective amount of PIM kinase inhibitor selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol- 4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

Also provided herein is a method for the treatment of multiple myeloma in a patient, the method comprising administering to the patient a therapeutically effective amount of a compound of formula (I), or a pharmaceutically acceptable salt thereof, and a therapeutically effective amount of a PIM kinase inhibitor, or a pharmaceutically acceptable salt thereof.

Also provided herein is a method for the treatment of multiple myeloma in a patient, the method comprising administering to the patient a therapeutically effective amount of a compound of formula (IV), or a pharmaceutically acceptable salt thereof, and a therapeutically effective amount of a PIM kinase inhibitor, or a pharmaceutically acceptable salt thereof.

Also provided herein is a method for the treatment of multiple myeloma in a patient, the method comprising administering to the patient a therapeutically effective amount of a compound with the following formula:

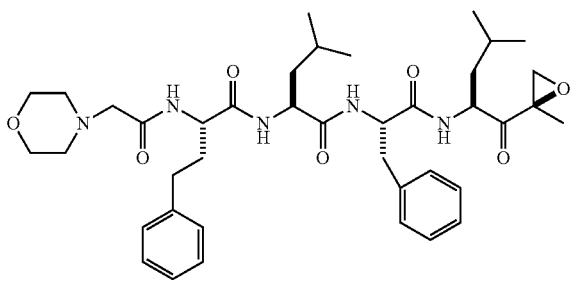 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of a PIM kinase inhibitor, or a pharmaceutically acceptable salt thereof.

Also provided herein is a method for the treatment of multiple myeloma in a patient, the method comprising administering to the patient a therapeutically effective amount of a compound with the following formula:

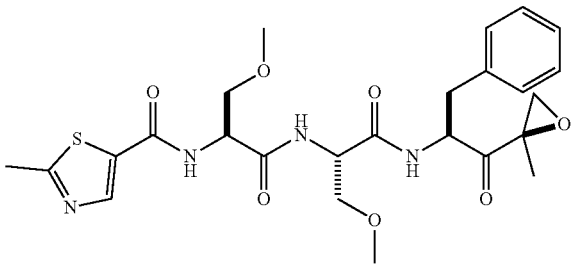 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, an a therapeutically effective amount of a PIM kinase inhibitor, or a pharmaceutically acceptable salt thereof.

Additionally, provided herein is a method for the treatment of multiple myeloma in a patient, the method comprising administering to the patient a therapeutically effective amount of a compound with the following formula:

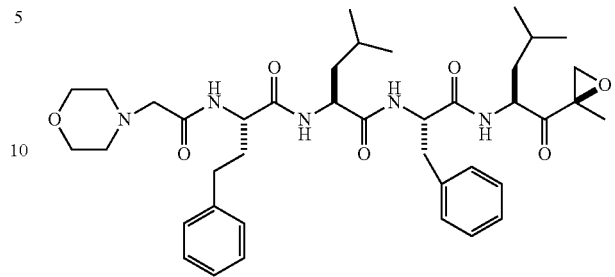

or a pharmaceutically acceptable salt thereof, and a therapeutically effective amount of PIM-2 selective kinase inhibitor, or a pharmaceutically acceptable salt thereof.

Additionally, provided herein is a method for the treatment of multiple myeloma in a patient, the method comprising administering to the patient a therapeutically effective amount of a compound with the following formula:

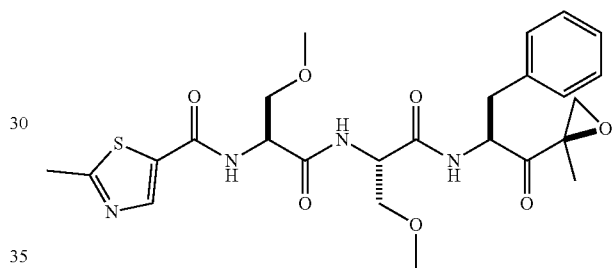

or a pharmaceutically acceptable salt thereof, and a therapeutically effective amount of PIM-2 selective kinase inhibitor, or a pharmaceutically acceptable salt thereof.

Aspects of the invention described as methods of treatment should also be understood to include first or subsequent "medical use" aspects of the invention or "Swiss use" of compositions for the manufacture of a medicament for treatment of the same disease or condition.

Multiple embodiments are contemplated for combination inventions described herein. For example, some aspects of the invention that are described as a method of treatment (or medical use) combining two or more compounds or agents, whether administered separately (sequentially or simultaneously) or in combination (co-formulated or mixed). For each aspect described in this manner, the invention further includes a composition comprising the two or more compounds or agents co-formulated or in admixture with each other; and the invention further includes a kit or unit dose containing the two or more compounds/agents packaged together, but not in admixture. Optionally, such compositions, kits or doses further include one or more carriers in admixture with one or both agents or co-packaged for formulation prior to administration to a subject. The reverse also is true: some aspects of the invention are described herein as compositions useful for therapy and containing two or more therapeutic agents. Equivalent methods and uses are specifically contemplated.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

BRIEF DESCRIPTION OF FIGURES

FIG. 2A is a graph that shows the effect of 100 M (Z)-5-(4-propoxybenzylidene)thiazolidine-2,4-dione and 1.98 nM carfilzomib, alone (left and middle bars, respectively) or in combination (right bar) on NIH-H929 cells. FIG. 2B is a graph that shows the effect of 100 μM (Z)-5-(4-propoxybenzylidene)thiazolidine-2,4-dione and 4.44 nM carfilzomib, alone (left and middle bars, respectively) and in combination (right bar) on NIH-H929 cells. FIG. 2C is a graph that shows the effect of the combination of 100 M (Z)-5-(4-propoxybenzylidene)thiazolidine-2,4-dione and 2.96 nM carfilzomib, alone (left and middle bars, respectively) and in combination (right bar) on U266 cells. FIG. 2D is a graph that shows the effect of 100 μM (Z)-5-(4-propoxybenzylidene)thiazolidine-2,4-dione and 6.66 nM carfilzomib, alone (left and middle bars, respectively) and in combination (right bar) on U266 cells.

DETAILED DESCRIPTION

Figure 1:
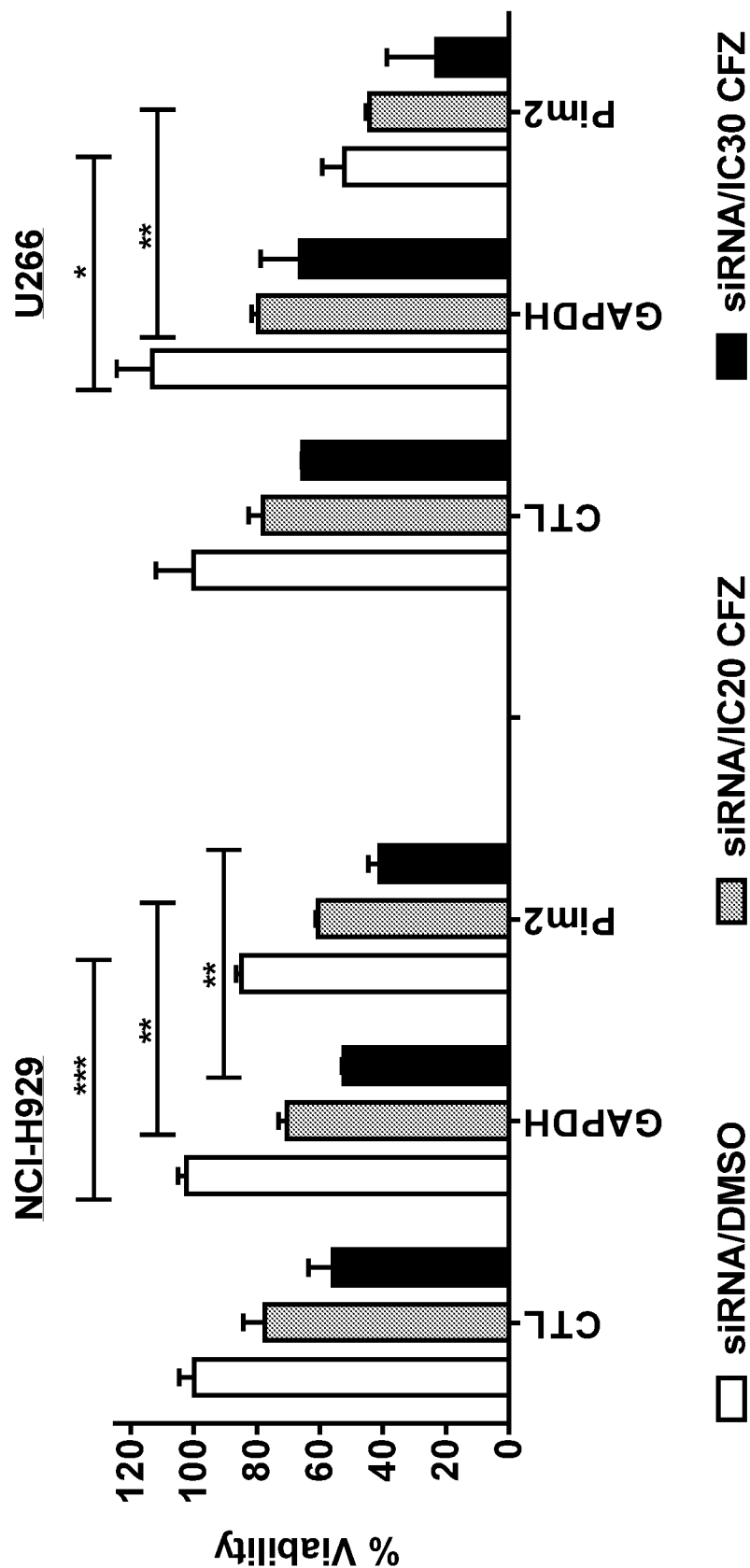
FIG. 1 is a graph that shows the effect of PIM-2 knockdown in combination with carfilzomib treatment on two cell lines.

This disclosure generally provides methods of treating a cancer in a patient using a peptide epoxyketone proteasome inhibitor in combination with a PIM kinase inhibitor.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

As used herein, chemical structures which contain one or more stereocenters depicted with dashed and bold bonds (i.e. ) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively. In some embodiments, an alkyl, alkenyl, and/or alkynyl group can be substituted with a halogen, such as fluorine.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The term "$C_{1-6}$hydroxyalkyl" refers to a $C_{1-6}$alkyl group substituted with a hydroxy group.

The terms "amine" and "amino" are art-recognized and refer to both unsubstituted and substituted amines and salts thereof, e.g., a moiety that can be represented by the general formulae:

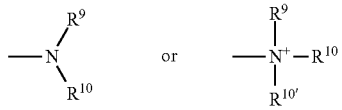

where $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In some embodiments, only one of $R^9$ or $R^{10}$ is a carbonyl, e.g., $R^9$, $R^{10}$, and the nitrogen together do not form an imide. In some embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning its protonated form has a pKa above 7.00.

The terms "amide" and "amido" are art-recognized as an amino-substituted carbonyl and include a moiety that can be represented by the general formula:

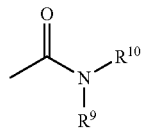

wherein $R^9$ and $R^{10}$ are as defined above. In some embodiments, the amide will not include imides, which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. In some embodiments, an aryl ring can be substituted with a halogen, such as fluorine.

The terms "carbocycle", "carbocyclyl", and "cycloalkyl" as used herein, refer to a 3- to 7-membered non-aromatic substituted or unsubstituted ring in which each atom of the ring is carbon. The terms "carbocycle", "carbocyclyl", and "cycloalkyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Carbocyclyls include cyclopropyl, cyclopentyl, cyclohexyl, cyclohexylmethyl, and 4-methylcyclohexyl. Examples of polycyclic carbocyclyls include bicyclo[2.2.1]heptanyl, norbornyl, and adamantyl.

The term "carbonyl" is art-recognized and includes moieties such as those represented by the general formulae:

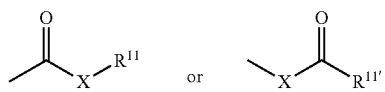

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen and $R^{11}$ is a hydrogen, the formula represents a "carboxylic acid".

The term "$C_{1-6}$heteroaralkyl", as used herein, refers to a $C_{1-6}$alkyl group substituted with a heteroaryl group.

The term "heteroaryl" includes substituted or unsubstituted aromatic 5- to 7-membered ring structures, for example, 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine, and pyrimidine, and the like. In some embodiments, a heteroaryl ring can be substituted with a halogen, such as fluorine.

The term "heteroatom" as used herein means an atom of any element other than carbon or hydrogen. For example, heteroatoms include nitrogen, oxygen, phosphorus, and sulfur.

The term "heterocyclyl" or "heterocyclic group" refers to substituted or unsubstituted non-aromatic 3- to 10-membered ring structures, for example, 3- to 7-membered rings, whose ring structures include one to four heteroatoms. The term "heterocyclyl" or "heterocyclic group" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "thioether" refers to an alkyl group, as defined above, having a sulfur moiety attached thereto. In some embodiments, the "thioether" is represented by —S alkyl. Representative thioether groups include methylthio, ethylthio, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, an alkyl, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety. It will be understood by those skilled in the art that the moieties substituted on the hydrocarbon chain can themselves be substituted, if appropriate. In some embodiments, the substituent is a halogen, such as fluorine.

In some embodiments, the compounds provided herein, or salts thereof, are substantially isolated or purified. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds, or salt thereof. Methods for isolating compounds and their salts are routine in the art.

The term "proteasome" as used herein is meant to include immuno- and constitutive proteasomes. In some embodiments, a method of the disclosure uses a compound that preferentially inhibits the immunoproteasome.

As used herein, the term "inhibitor" is meant to describe a compound that blocks or reduces an activity of an enzyme or system of enzymes, receptors, or other pharmacological target (for example, inhibition of proteolytic cleavage of standard fluorogenic peptide substrates such as suc-LLVY-AMC (N-Succinyl-Leu-Leu-Val-Tyr-(7-amino-4-methylcoumarin)), Boc-LLR-AMC (tert-butyloxycarbonyl-Leu-Leu-Arg-(7-amino-4-methylcoumarin)), and Z-LLE-AMC (benzyloxycarbonyl-Leu-Leu-Glu-(7-amino-4-methylcoumarin)), inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting one or more symptoms, clinical signs, and underlying pathology of a condition in a manner to improve or stabilize a patient's condition.

Methods of Use

Combination drug therapy is the use of two or more pharmacologic agents administered either separately or in a single dose formulation. The use of combinations can be employed to treat cancer in a patient. For example, the cancer can be a hematological malignancy. In some embodiments, the combinations can be used to increase the efficacy of the individual components, to overcome resistance to a particular agent, or to treat a refractory disease.

Provided herein is a method for treating a cancer in a patient, the method including administering to the patient a therapeutically effective amount of a peptide epoxyketone proteasome inhibitor as provided herein (e.g., a compound of formula (I) or a compound of formula (IV)) and a therapeutically effective amount of a PIM kinase inhibitor.

As used herein, the term "cancer" includes, but is not limited to, blood borne and solid tumors. Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), pancreatic adenocarcinoma, colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, lung cancer, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the hematopoietic and lymphoid tissues are characterized by an increase in cell proliferation, or a particular type of cell. The chronic myeloproliferative diseases (CMPDs) are clonal hematopoietic stem cell disorders characterized by proliferation in the bone marrow of one or more of the myeloid lineages, resulting in increased numbers of granulocytes, red blood cells and/or platelets in the peripheral blood. CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease.

Myelodysplastic/myeloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages.

Myelodysplastic syndromes (MDS) refer to a group of hematopoietic stem cell disorders characterized by dysplasia and ineffective hematopoiesis in one or more of the major myeloid cell lines. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal hematological non-mast-cell-lineage disease (SM-AHNMD), aggressive systemic mastocytosis (ASM), mast cell leukemia (MCL), mast cell sarcoma (MCS) and extracutaneous mastocytoma.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. *Cancer Res*. (2006) 66:5461-5468). In some embodiments, a composition provided herein can be administered to a patient with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor, and non-specified dendritic cell sarcoma.

In some embodiments, the cancer is one selected from bone cancer, gynecological cancer, breast cancer, hematological malignancy, skin cancer, liver cancer, kidney cancer, pancreatic cancer, brain cancer, lung cancer, and prostate cancer. For example, the cancer can be a hematological malignancy.

Provided herein is a method for treating a hematological malignancy in a patient, the method including administering to the patient a therapeutically effective amount of a peptide epoxyketone proteasome inhibitor as provided herein (e.g., a compound of formula (I) or a compound of formula (IV)) and a therapeutically effective amount of a PIM kinase inhibitor.

The term "hematological malignancy" as used herein is meant to include cancers that affect one or more of the blood, bone marrow, and lymph nodes, such as acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms. In some embodiments, the hematological malignancy is selected from AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms. For example, the hematological malignancy can be B-cell lymphoma or multiple myeloma. In some embodiments, the hematological malignancy is multiple myeloma. For example, multiple myeloma can include refractory and/or refractory multiple myeloma.

The term "refractory" as used herein is meant to refer to cancers that do not respond to treatment. For example, the treatment involved may be chemotherapy or radiation treatment. The cancer may be refractory at the start of treatment, or it may become refractory during treatment. In some embodiments, the methods of the disclosure are directed to treatment of a cancer that is refractory. In some embodiments, the cancer can be a hematological malignancy.

The term "resistant" as used herein is meant to refer to cancers that do not respond to drug treatment. The cancer may be resistant at the start of treatment, or it may become resistant during treatment. In some embodiments, the methods of the disclosure are directed to treatment of a cancer that is resistant. In some embodiments, the cancer can be a hematological malignancy.

A "patient" as used herein refers to a mammal. For example, the mammal may be a mouse, rat, guinea pig, dog, monkey, such as a cynomolgous monkey, or chimpanzee. Another example of a mammal is a human.

In some embodiments, the patient is one in whom PIM-2 is overexpressed.

In some embodiments, the methods described herein use a peptide epoxyketone proteasome inhibitor of formula (I):

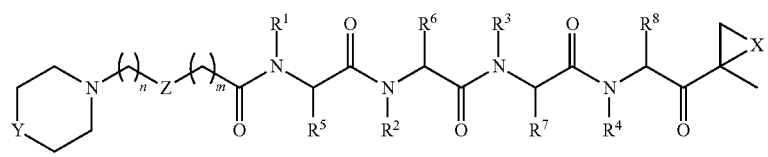

or a pharmaceutically acceptable salt thereof,
wherein X is O, NH, or N-alkyl; Y is NH, N-alkyl, O, or $C(R^9)_2$; Z is O or $C(R^9)_2$; $R^1$, $R^2$, $R^3$, and $R^4$ are all hydrogen; each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether; $R^{10}$ and $R^{11}$ are independently selected from hydrogen and $C_{1-6}$alkyl, or $R^{10}$ and $R^{11}$ together form a 3- to 6-membered carbocyclic or heterocyclic ring; $R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; m is an integer from 0 to 2; n is an integer from 0 to 2, preferably 0 or 1. In some embodiments, $R^5$, $R^6$, $R^7$, and $R^8$ are independently selected from $C_{1-6}$alkyl, $C_{1-6}$ hydroxyalkyl, and $C_{1-6}$aralkyl. In some embodiments, $R^6$ and $R^8$ are each independently selected from $C_{1-6}$alkyl, $C_{1-6}$hydroxyalkyl, and $C_{1-6}$aralkyl. In some embodiments, $R^6$ and $R^8$ are each independently a $C_{1-6}$alkyl, such as isobutyl. In some embodiments, $R^5$ and $R^7$ are each independently selected from $C_{1-6}$alkyl, $C_{1-6}$hydroxyalkyl, and $C_{1-6}$aralkyl. In some embodiments, $R^5$ and $R^7$ are each independently a $C_{1-6}$aralkyl. In some embodiments, $R^5$ is a $(C_{1-6}$alkyl)phenyl, such as phenethyl. In some embodiments, $R^7$ is a $(C_{1-6}$alkyl)phenyl, such as phenylmethyl. In some embodiments, $R^5$ and $R^7$ are independently $C_{1-6}$aralkyl and $R^6$ and $R^8$ are independently $C_{1-6}$alkyl. In some embodiments, $R^9$ is selected from hydrogen, $C_{1-6}$alkyl, $C_{1-6}$alkoxyalkyl, and $C_{1-6}$aralkyl. In some embodiments, $R^9$ is a $C_{1-6}$alkyl, such as $CH_3$. In some embodiments, $R^9$ is a hydrogen. In some embodiments, $R^5$, $R^6$, $R^7$, and $R^8$ are independently selected from $C_{1-6}$alkyl, $C_{1-6}$hydroxyalkyl, and $C_{1-6}$aralkyl; and $R^9$ is a hydrogen. In some embodiments, n is 0. In some embodiments, n is 1. In some embodiments, m is 0. In some embodiments, m is 1. In some embodiments, m is 2. In some embodiments, Z is O. In some embodiments, Z is $C(R^9)_2$. In some embodiments, Z is $CH_2$; and m and n are both 0. In some embodiments, Z is $CH_2$, m is 0, and n is 2. In some embodiments, Z is O, m is 1, and n is 2. In some embodiments, X is O. In some embodiments, Y is N—$CH_3$, O, or $CH_2$. In some embodiments, Y is O.

In some embodiments, a compound of formula (I) can be a compound of formula (II):

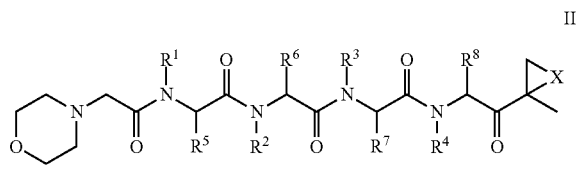

wherein X is selected from O, NH, and N-alkyl; $R^1$, $R^2$, $R^3$, and $R^4$ are all hydrogen; $R^5$, $R^6$, $R^7$, and $R^8$ are independently selected from hydrogen, $C_{1-6}$alkyl, $C_{1-6}$ hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether. In some embodiments, $R^6$ and $R^8$ are each independently selected from $C_{1-6}$alkyl, $C_{1-6}$alkoxyalkyl, and $C_{1-6}$aralkyl. In some embodiments, $R^6$ and $R^8$ are each independently $C_{1-6}$alkyl, such as isobutyl. In some embodiments, $R^5$ and $R^7$ are each independently selected from $C_{1-6}$alkyl, $C_{1-6}$alkoxyalkyl, and $C_{1-6}$aralkyl. In some embodiments, $R^5$ and $R^7$ are each independently a $C_{1-6}$aralkyl. In some embodiments, $R^5$ is a $(C_{1-6}$alkyl)phenyl, such as phenethyl. In some embodiments, $R^7$ is a $(C_{1-6}$alkyl)phenyl, such as phenylmethyl. In some embodiments, X is O.

In some embodiments, a compound of formula (I) can be a compound of formula (III):

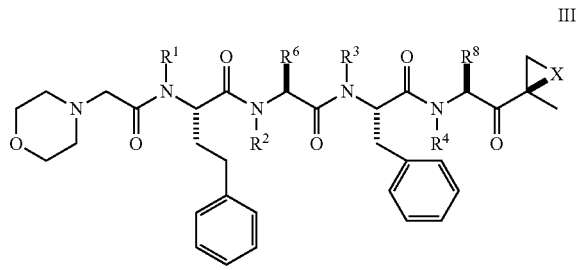

wherein X is O, NH, or N-alkyl; $R^1$, $R^2$, $R^3$, and $R^4$ are all hydrogen; $R^6$ and R are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether. In some embodiments, $R^6$ and $R^8$ are each independently selected from $C_{1-6}$alkyl, $C_{1-6}$alkoxyalkyl, and $C_{1-6}$aralkyl. In some embodiments, $R^6$ and $R^8$ are each independently a $C_{1-6}$alkyl, such as isobutyl. In some embodiments, X is O.

Non-limiting examples of compounds of formulas (I), (II), and/or (III) include:

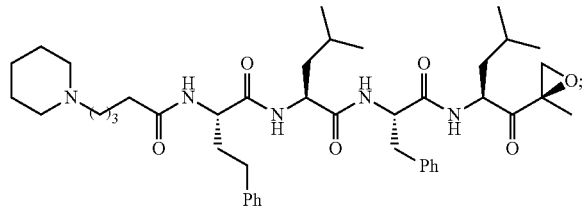

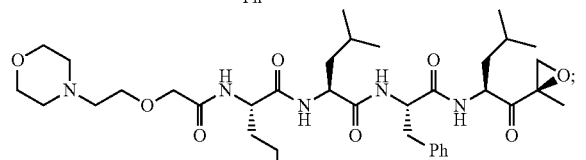

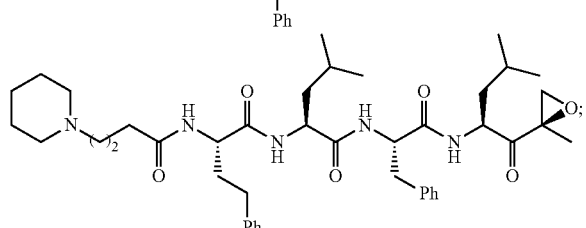

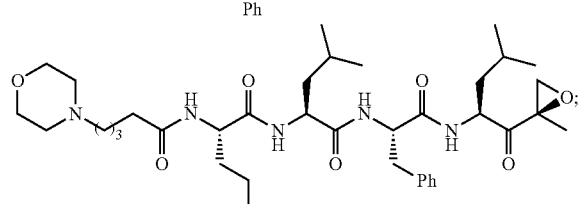

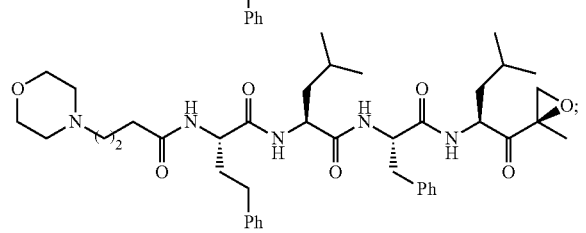

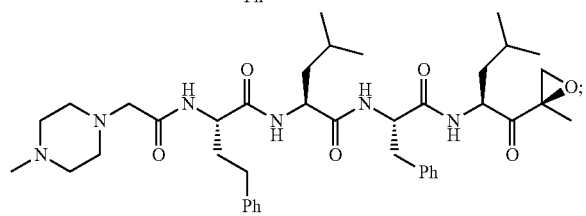

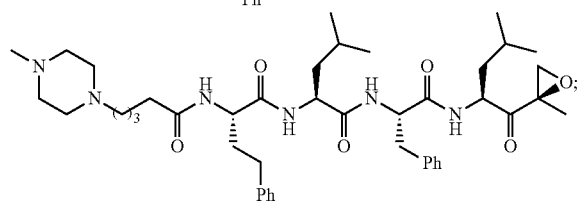

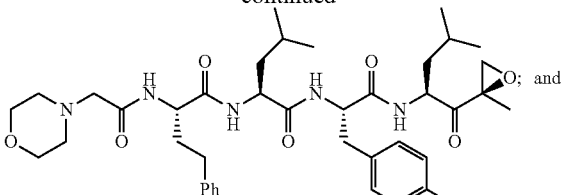

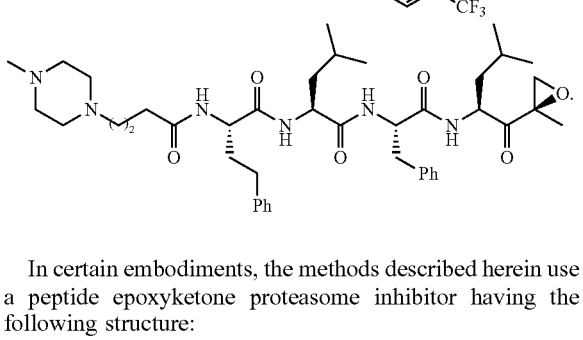

In certain embodiments, the methods described herein use a peptide epoxyketone proteasome inhibitor having the following structure:

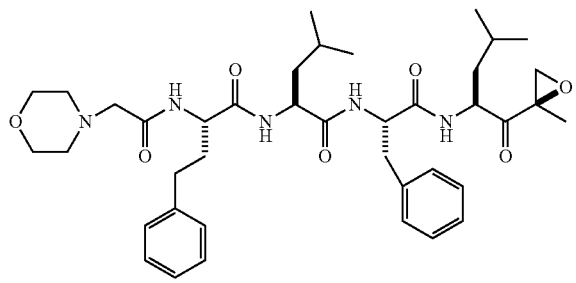 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt form thereof.

In some embodiments, the methods described herein use a compound of formula (IV) or a pharmaceutically acceptable salt thereof:

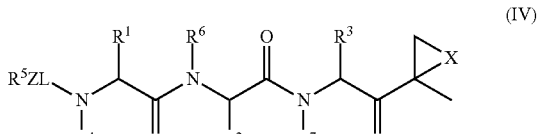

(IV)

wherein L is selected from C=O, C=S, and SO$_2$; X is selected from O, S, NH, and N—C$_{1-6}$alkyl; Z is absent, C$_{1-6}$alkyl, or C$_{1-6}$alkoxy; $R^1$, $R^2$, and $R^3$ are each independently selected from hydrogen, C$_{1-6}$alkyl, C$_{1-6}$alkenyl, C$_{1-6}$alkynyl, C$_{1-6}$hydroxyalkyl, C$_{1-6}$alkoxyalkyl, aryl, C$_{1-6}$aralkyl, heteroaryl, heterocyclyl, C$_{1-6}$heterocycloalkyl, C$_{1-6}$heteroaralkyl, carbocyclyl, and C$_{1-6}$carbocyclylalkyl; $R^4$ is selected from hydrogen, C$_{1-6}$aralkyl, and C$_{1-6}$alkyl; $R^5$ is heteroaryl; and $R^6$ and $R^7$ are independently selected from hydrogen, C$_{1-6}$alkyl, and C$_{1-6}$aralkyl. In some embodiments, Z is absent. In some embodiments, $R^4$, $R^6$, and $R^7$ are independently selected from hydrogen and methyl. In some embodiments, L is C=O. In some embodiments, L is SO$_2$. In some embodiments, $R^1$, $R^2$, and $R^3$ are independently selected from hydrogen, C$_{1-6}$alkyl, C$_{1-6}$alkenyl, C$_{1-6}$alkynyl, C$_{1-6}$hydroxyalkyl, C$_{1-6}$alkoxyalkyl, C$_{1-6}$aralkyl, C$_{1-6}$heterocycloalkyl, C$_{1-6}$heteroaralkyl, and C$_{1-6}$carbocyclylalkyl. In some embodiments, $R^1$, $R^2$, and $R^3$ are all different. In some embodiments, $R^1$, $R^2$, and $R^3$ are independently C$_{1-6}$alkyl.

For example, $R^1$, $R^2$, and $R^3$ can be independently selected from methyl, ethyl, propyl, isopropyl, butyl, sec-butyl, and isobutyl. In certain embodiments, any of $R^1$, $R^2$, and $R^3$ are independently propargyl. In some embodiments, any of $R^1$, $R^2$, and $R^3$ are independently $C_{1-6}$hydroxyalkyl. For example, any of $R^1$, $R^2$, and $R^3$ can be independently selected from hydroxymethyl and hydroxyethyl. In some embodiments, any of $R^1$, $R^2$, and $R^3$ are independently $C_{1-6}$alkoxyalkyl. For example, any of $R^1$, $R^2$, and $R^3$ can be independently selected from methoxymethyl and methoxyethyl. In some embodiments, any of $R^1$, $R^2$, and $R^3$ are independently $C_{1-6}$heteroaralkyl. For example, any of $R^1$, $R^2$, and $R^3$ are independently selected from imidazolylmethyl, pyrazolylmethyl, thiazolylmethyl, and pyridylmethyl. In certain embodiments, any of $R^1$, $R^2$, and $R^3$ are independently cyclohexylmethyl. In some embodiments, at least one of $R^1$ and $R^2$ is selected from $C_{1-6}$hydroxyalkyl and $C_{1-6}$alkoxyalkyl. In some embodiments, at least one of $R^1$ and $R^2$ is $C_{1-6}$alkoxyalkyl. For example, at least one of $R^1$ and $R^2$ can be selected from methoxymethyl and methoxyethyl. In some embodiments, $R^1$ and $R^2$ are methoxymethyl. In some embodiments, $R^3$ is selected from $C_{1-6}$alkyl and $C_{1-6}$aralkyl. In some embodiments, $R^3$ is $C_{1-6}$alkyl. For example, $R^3$ can be selected from methyl, ethyl, isopropyl, sec-butyl, and isobutyl. In certain embodiments, $R^3$ is isobutyl. In some embodiments, $R^3$ is $C_{1-6}$aralkyl. For example, $R^3$ can be phenylmethyl. In some embodiments, $R^3$ is (4-methoxy)phenylmethyl. In some embodiments, $R^1$ and $R^2$ are methoxymethyl and $R^3$ is (4-methoxy)phenylmethyl. In some embodiments, $R^5$ is 5- or 6-membered heteroaryl. In some embodiments, $R^5$ is selected from isoxazole, isothiazole, furan, thiophene, oxazole, thiazole, pyrazole, or imidazole. In some embodiments, $R^5$ is selected from isoxazole, furan, or thiophene. In some embodiments, $R^5$ is furan or thiophene. In some embodiments, $R^5$ is unsubstituted furan-3-yl or thien-2-yl. In some embodiments, $R^5$ is isoxazol-3-yl or isoxazol-5-yl. In some embodiments, $R^5$ is isoxazol-3-yl that has a substituent at the 5-position. In some embodiments, $R^5$ is isoxazol-5-yl that has a substituent at the 3-position. In some embodiments, the 3- or 5-position substituent is selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, $(C_{1-6}$alkyl$)_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl. In some embodiments, the 3- or 5-position substituent is selected from methyl, ethyl, isopropyl, and cyclopropylmethyl. In some embodiments, the 3- or 5-position substituent is selected from $C_{1-6}$heteroaralkyl and $C_{1-6}$heterocycloalkyl. In certain embodiments, the 3- or 5-position substituent is 1,2,4-triazol-5-ylmethyl. In certain embodiments, the 3- or 5-position substituent is azetidin-1-ylmethyl. In some embodiments, the 3- or 5-position substituent is

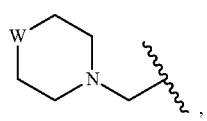

wherein W is O, NR, or $CH_2$, and R is H or $C_{1-6}$alkyl. In some embodiments, W is O. In some embodiments, the 3- or 5-position substituent is selected from $C_{1-6}$alkoxy and $C_{1-6}$alkoxyalkyl. In some embodiments, the 3- or 5-position substituent is selected from methoxy, ethoxy, methoxymethyl, and methoxyethyl. In some embodiments, the 3- or 5-position substituent is selected from carboxylic acid, aminocarboxylate, $C_{1-6}$alkylaminocarboxylate, $(C_{1-6}$alkyl$)_2$aminocarboxylate, or $C_{1-6}$alkylcarboxylate. In certain embodiments, the 3- or 5-position substituent is methyl carboxylate. In some embodiments, $R^5$ is a substituted or unsubstituted thiazole. For example, $R^5$ can be a substituted thiazole such as 2-methylthiazole.

Non-limiting examples of compounds of formula (IV) include:

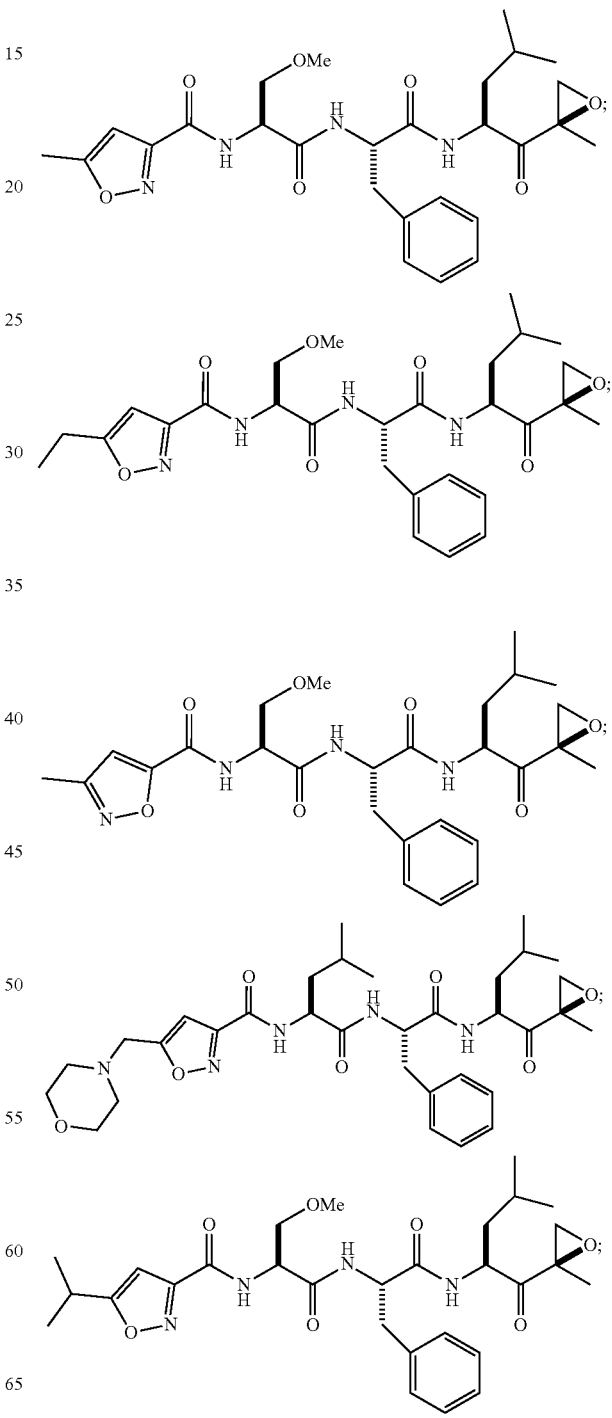

-continued
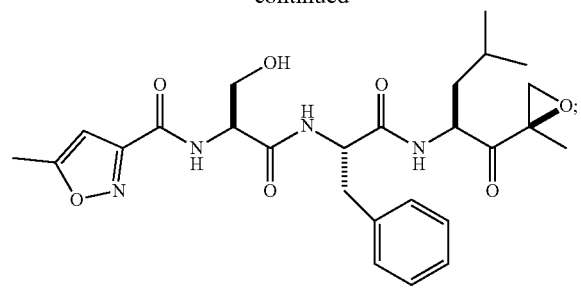
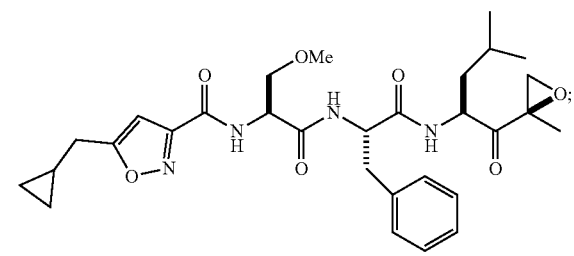
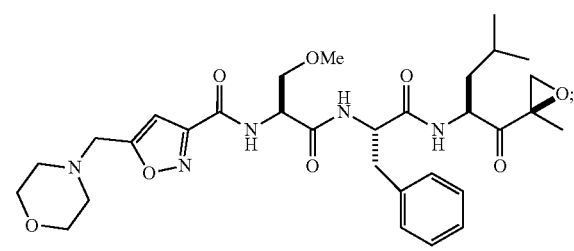
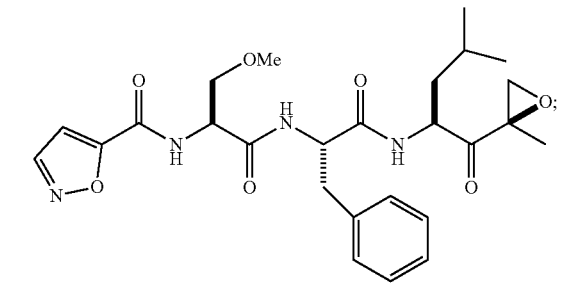
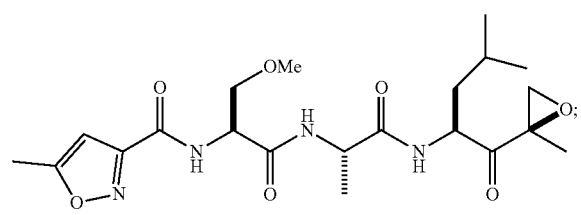
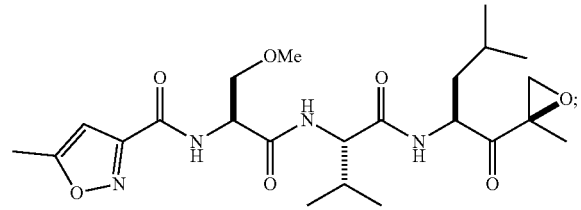
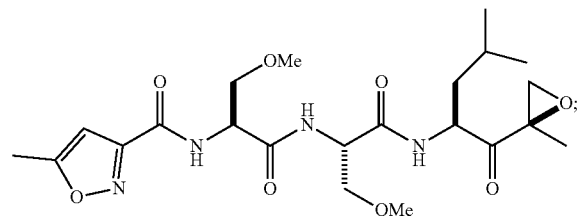
-continued
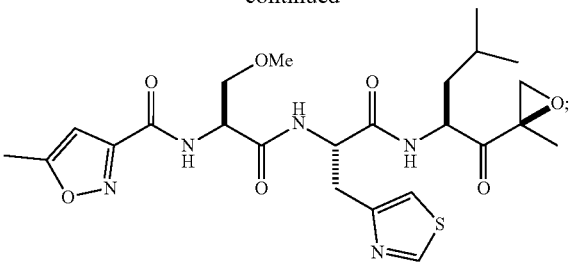
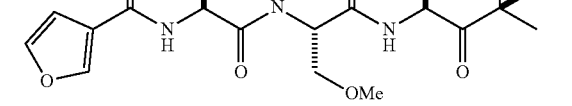
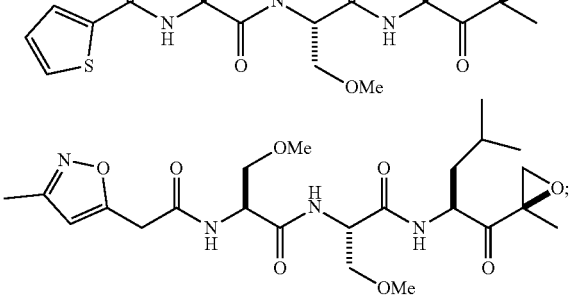
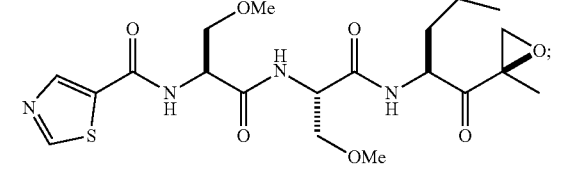
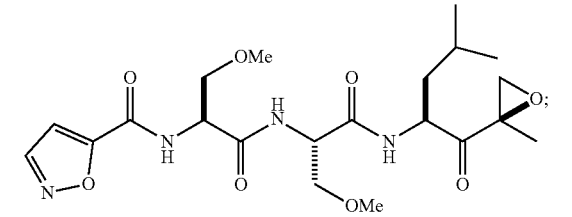
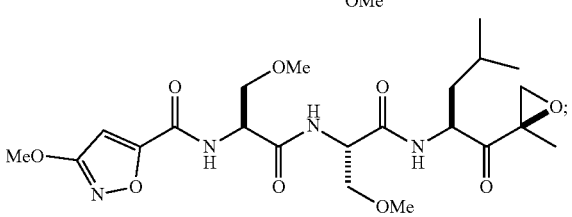

27
-continued
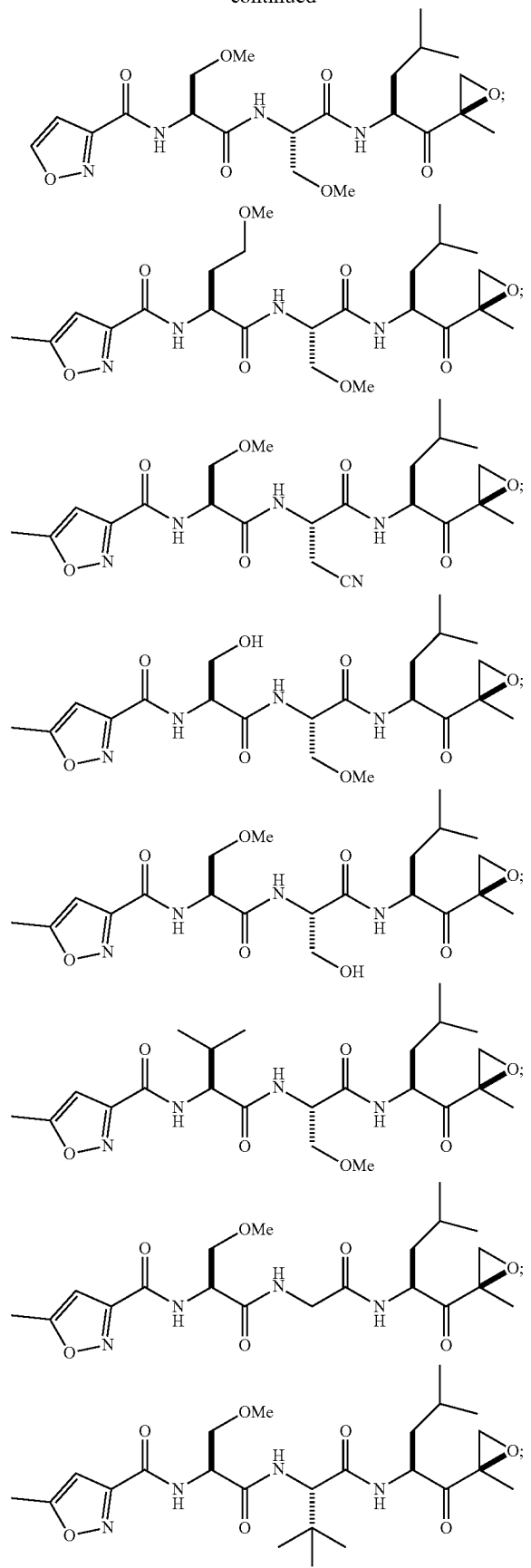
28
-continued
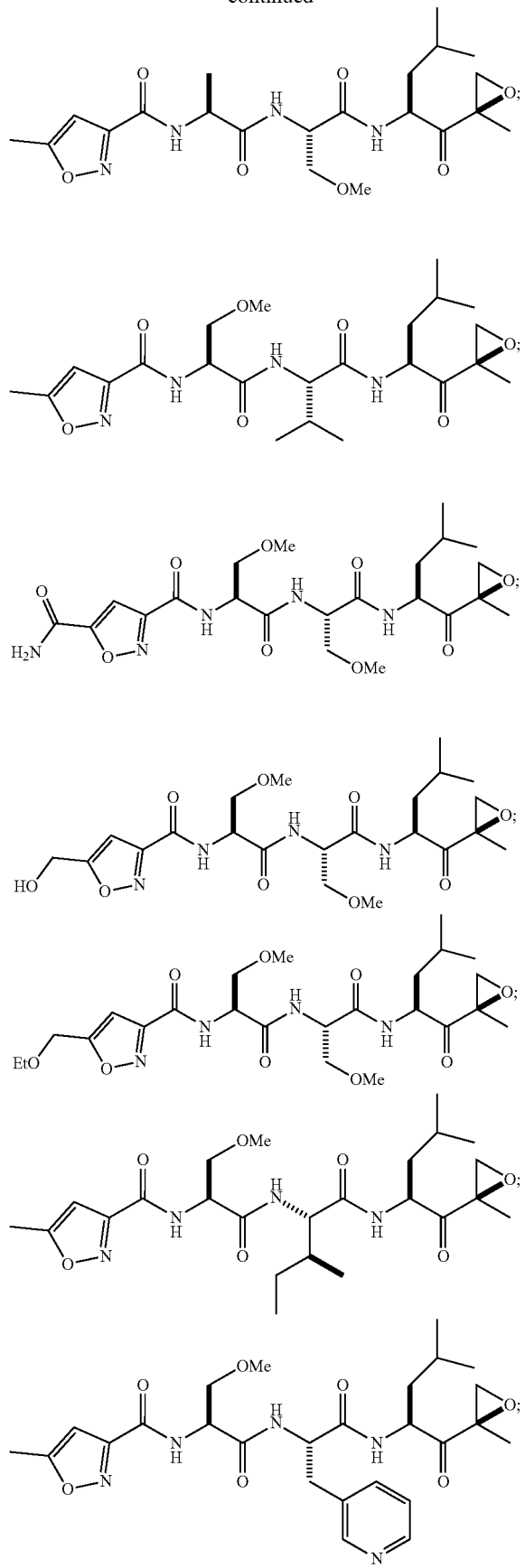

-continued
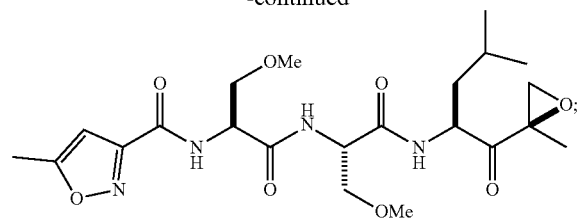
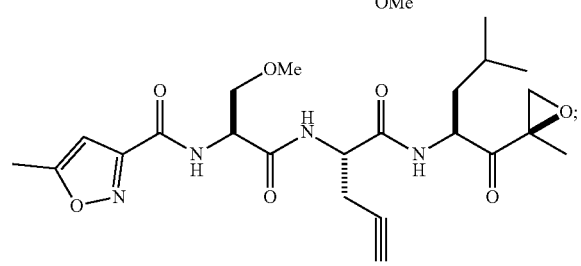
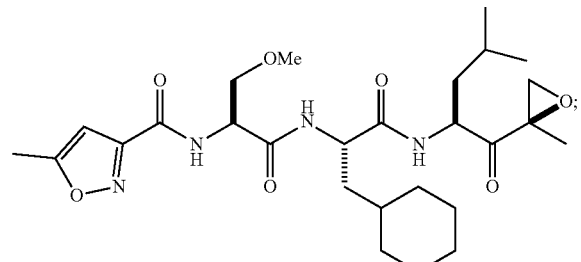
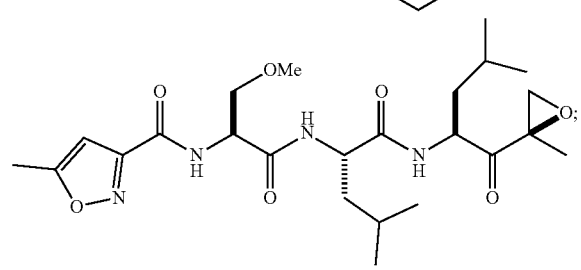
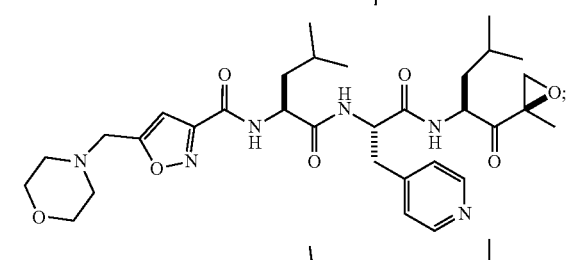
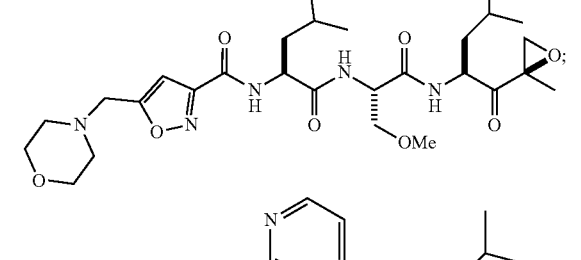
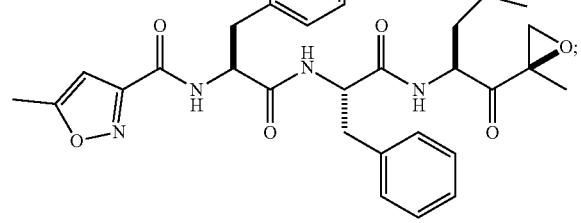
-continued
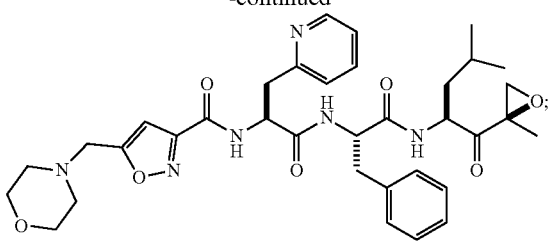
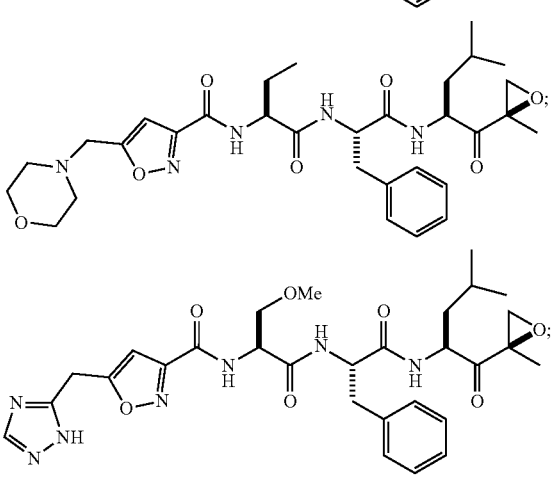
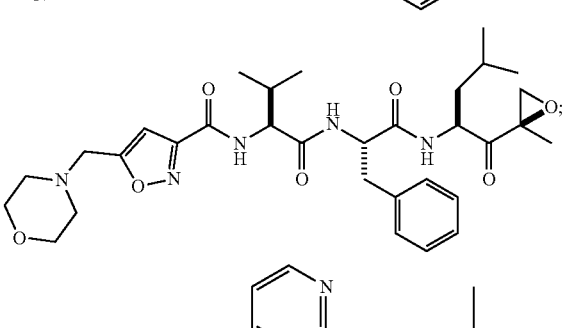
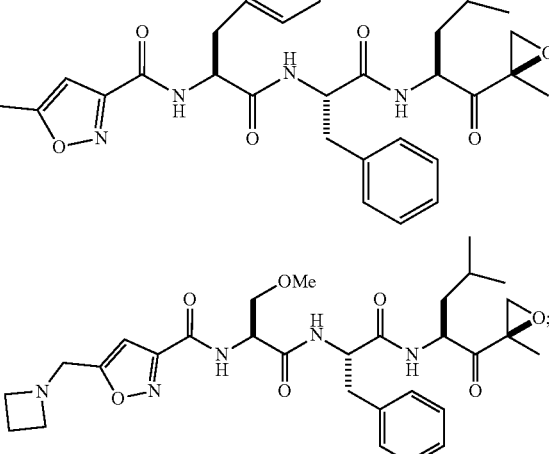
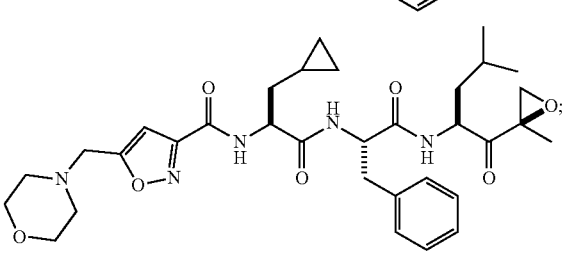

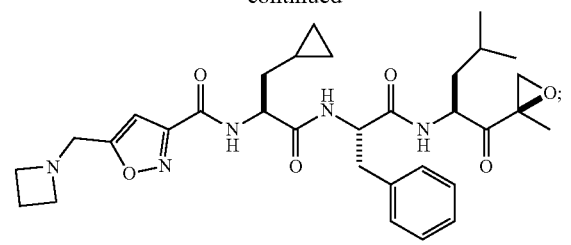
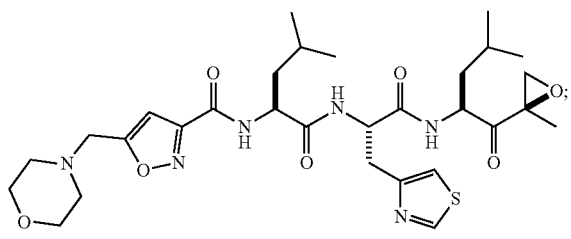
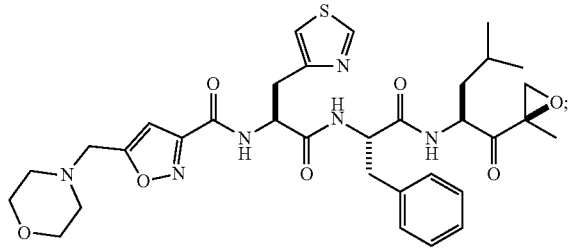
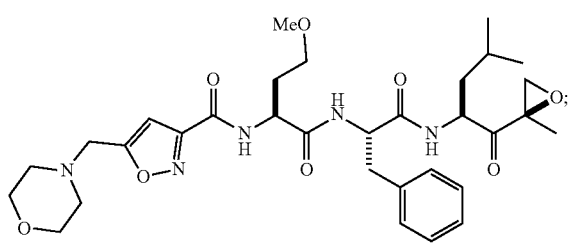
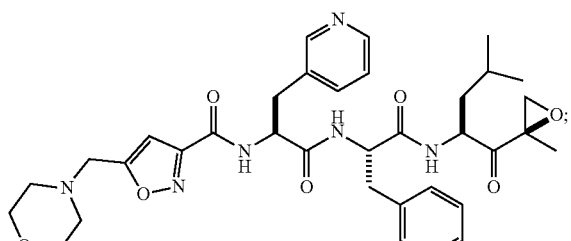
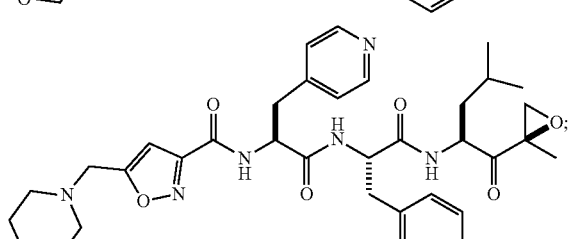
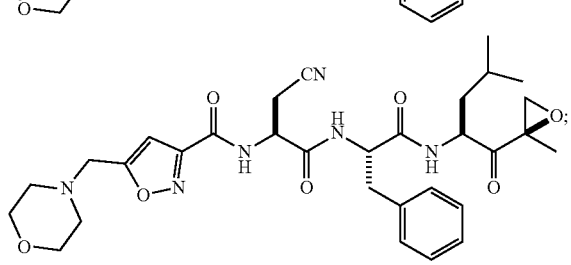
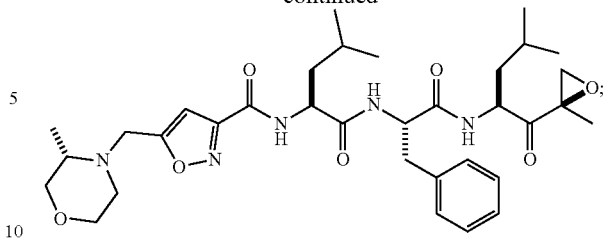
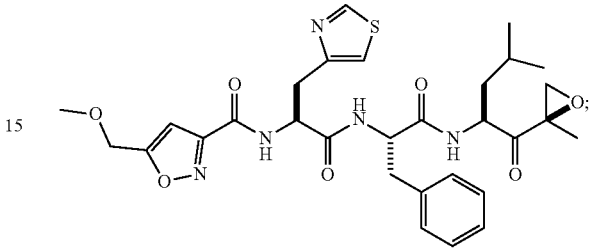
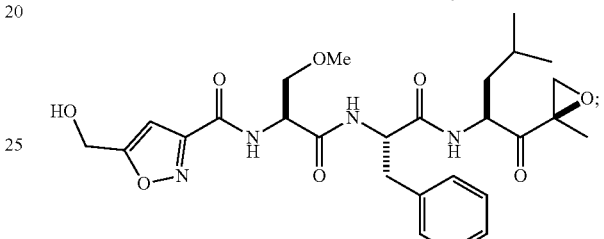
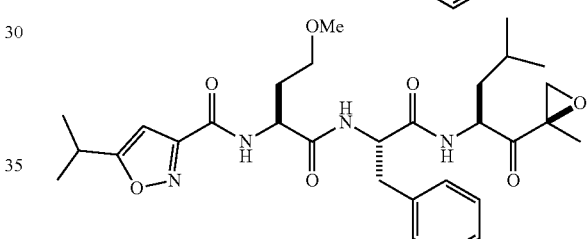
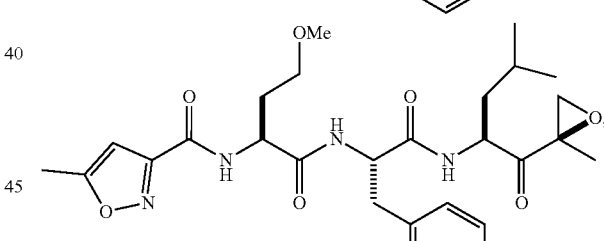
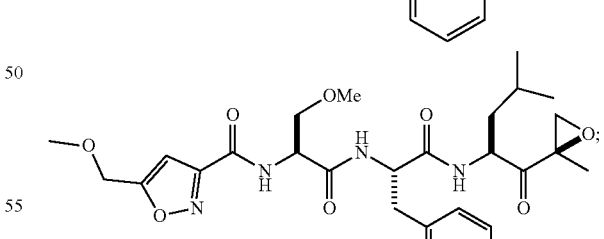
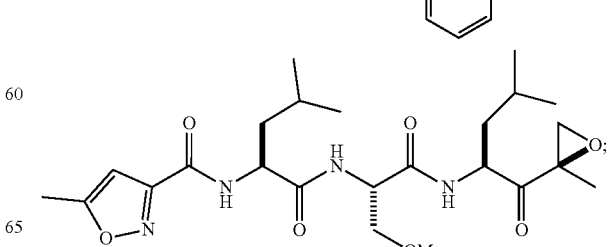

33
-continued
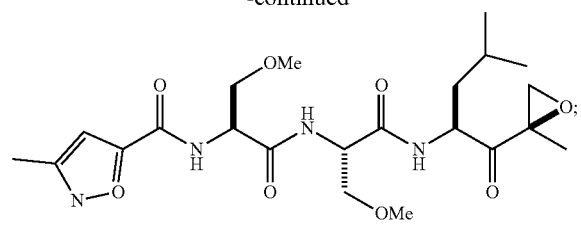
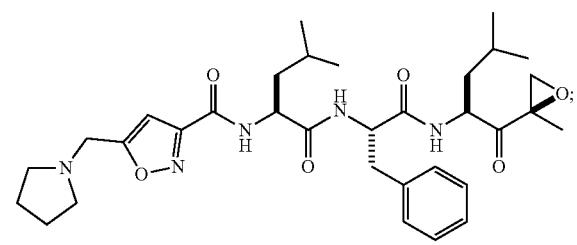
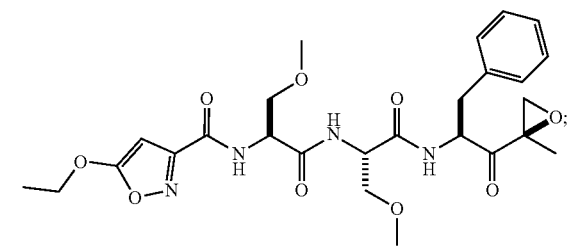
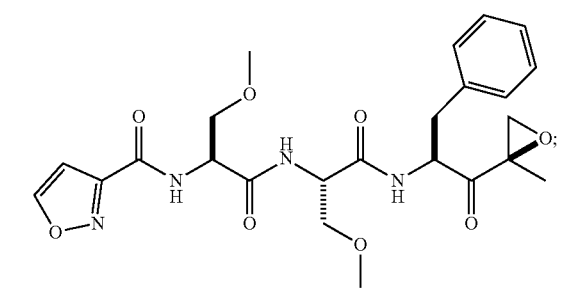
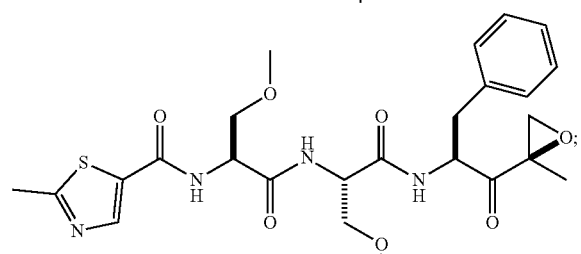
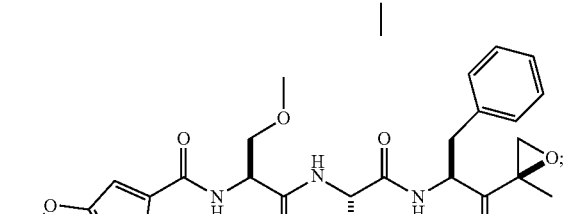
34
-continued
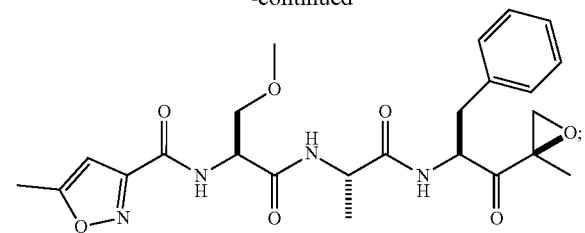
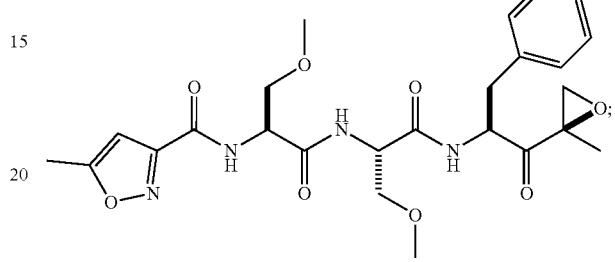
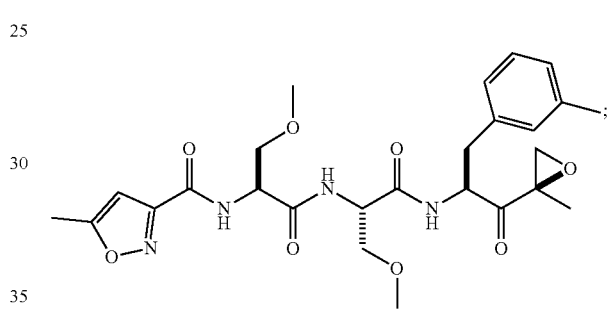
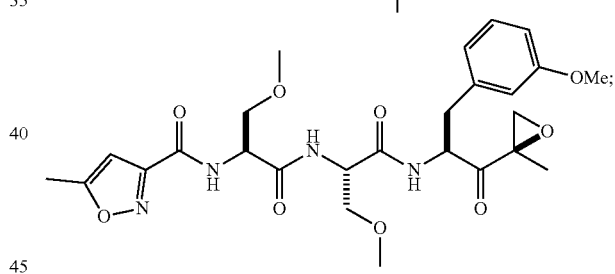
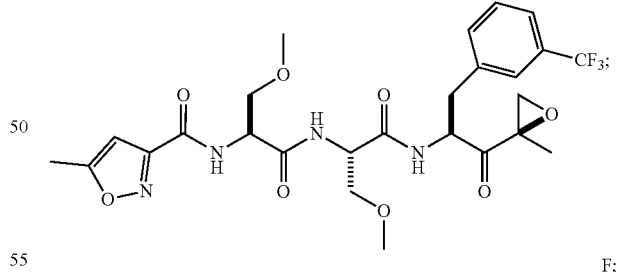
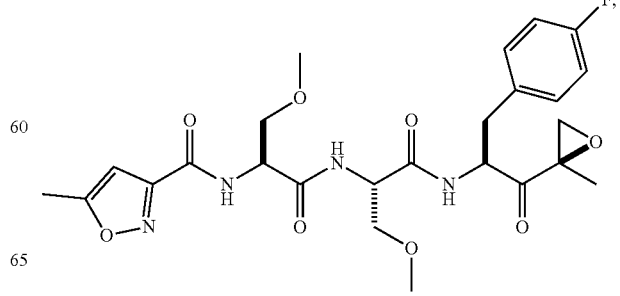

-continued

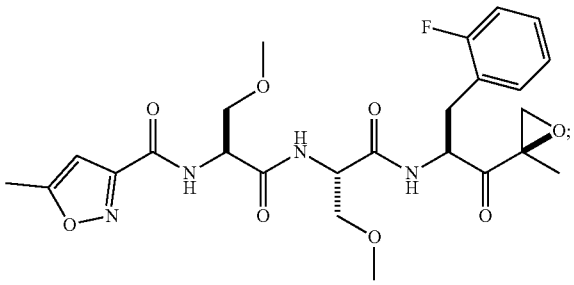

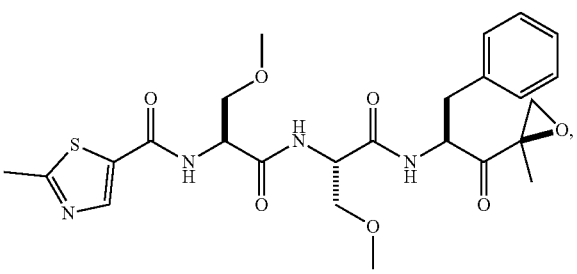 [SMILES: COC[C@H](NC(=O)c1cnc(C)s1)C(=O)N[C@@H](COC)C(=O)N[C@@H](Cc1ccccc1)C(=O)[C@@]1(C)CO1]

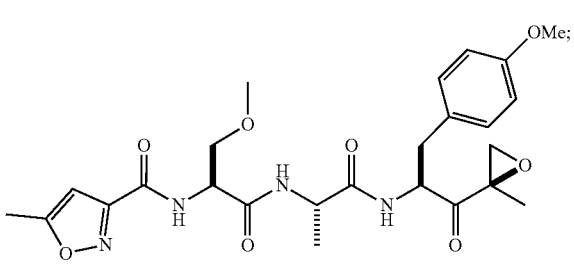

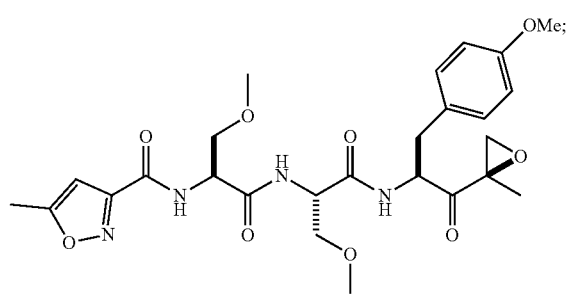

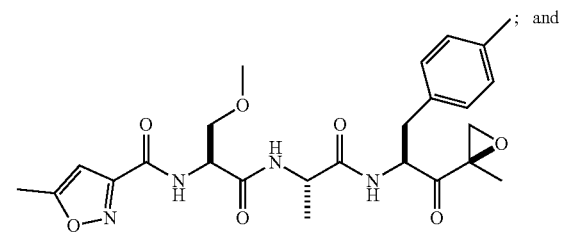

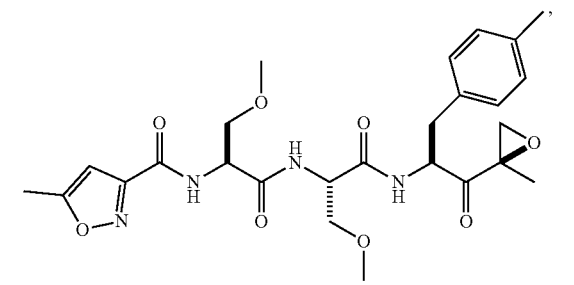

or a pharmaceutically acceptable salt thereof.

In some embodiments, the methods described herein use a compound that has the structure:

or a pharmaceutically acceptable salt thereof.

A Proviral integration Moloney (PIM) (PIM) kinase inhibitor as provided herein can be any compound that inhibits the action of a PIM kinase. For example, the compound can inhibit one or more of the serine/threonine kinases encoded by a PIM gene or protooncogene. In some embodiments, the serine/threonine kinase is one of three isoforms: PIM-1, PIM-2, and PIM-3. In some embodiments, the methods of the disclosure are directed to the treatment of cancers using a PIM kinase inhibitor. In some embodiments, the PIM kinase inhibitor is selective for one or more kinases selected from the group consisting of: PIM-1, PIM-2, and PIM-3. In some embodiments, the PIM kinase inhibitors is a pan-PIM inhibitor and inhibits each of PIM-1, PIM-2, and PIM-3. In some embodiments, the PIM kinase inhibitor is selective for PIM-1. In some embodiments, the PIM kinase inhibitor is selective for PIM-2. In some embodiments, the PIM kinase inhibitor is selective for PIM-3. In some embodiments, the PIM kinase inhibitor is a dual PIM-1/PIM-2 inhibitor. Examples of PIM kinase inhibitors can be found in: WO 2009/064486 and WO 2012/145617. Further contemplated PIM kinase inhibitors include those found in US20140031360, WO2012/129338, WO2012/148775, WO2013/130660 and WO2014/022752, the disclosures of which are each incorporated by reference in their entirety.

As used herein, the term "selective" indicates a greater effect for one measured value over another, comparable measured value. For example, a PIM kinase inhibitor that is selective for inhibition of PIM-2 over PIM-1 kinase means that the compound effects a defined amount of PIM-2 kinase inhibition at the same or lesser dose as that used to effect the same defined amount of PIM-1 kinase inhibition. A PIM-2 selective kinase inhibitor is one that is selective for inhibition of PIM-2 over the other isoforms PIM-1 and PIM-3.

Non-limiting examples of PIM kinase inhibitors include the following compounds:

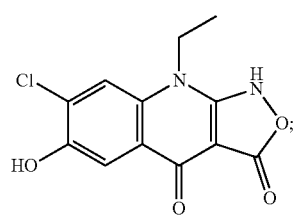

7-chloro-9-ethyl-6-hydroxyisoxazolo[3,4-b]quinoline-3,4(1H,9H)-dione

-continued

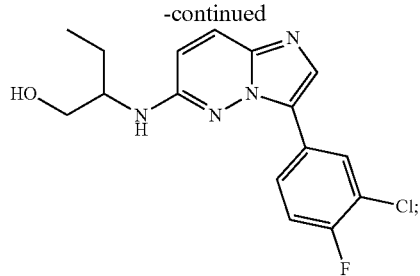

2-[[3-(3-chloro-4-fluorophenyl)imidazo[1,2-b]pyridazin-6-yl]amino]butan-1-ol

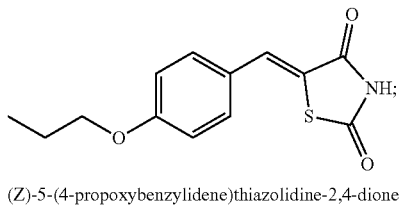

(Z)-5-(4-propoxybenzylidene)thiazolidine-2,4-dione

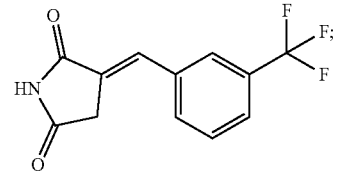

(Z)-5-(3-Trifluoromethylbenzylidene)thiazolidine-2,4-dione

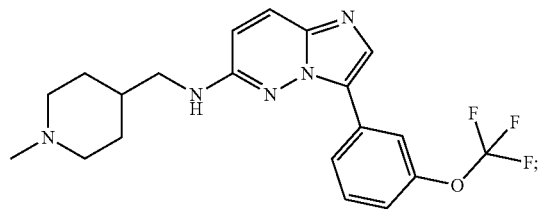

N-((1-methylpiperidin-4-yl)methyl)-3-(3-(trifluoromethoxy)phenyl)imidazo[1,2-b]pyridazin-6-amine

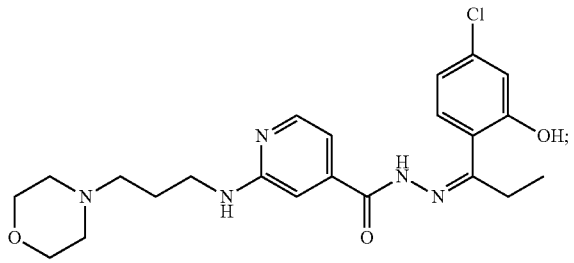

N'-(1-(4-Chloro-4-hydroxyphenyl)propylidene)-2-((3-(morpholinopropyl)amino)isonicotinohydrazide

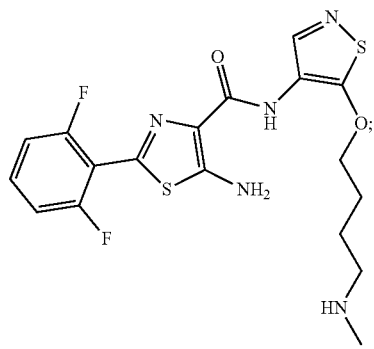

5-amino-2-(2,6-difluorophenyl)-N-(5-(4-(methylamino)butoxy)isothiazol-4-yl)thiazole-4-carboxamide -continued

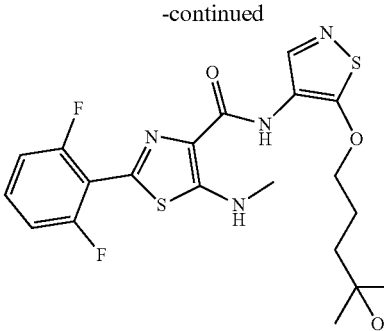

2-(2,6-difluorophenyl)-N-(5-(4-hydroxy-4-methylpentyloxy)isothiazol-4-yl)-5-(methylamino)thiazole-4-carboxamide

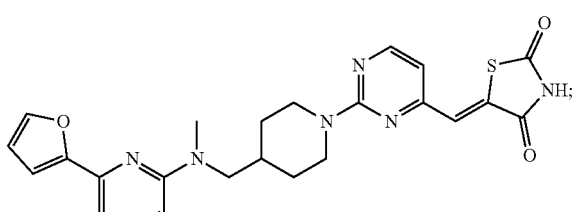

(Z)-5-((2-(4-(((6-(furan-2-yl)pyridin-2-yl)methylamino)methyl)piperidin-1-yl)pyrimidin-4-yl)methylene)thiazolidine-2,4-dione

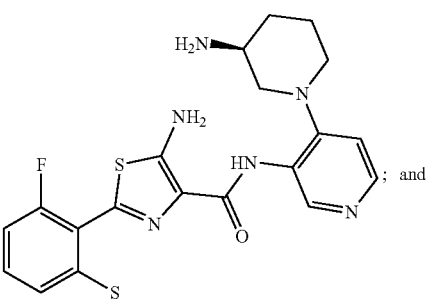

(S)-5-amino-N-(4-(3-aminopiperidin-1-yl)pyridin-3-yl)-2-(2,6-difluorophenyl)thiazole-4-carboxamide; and

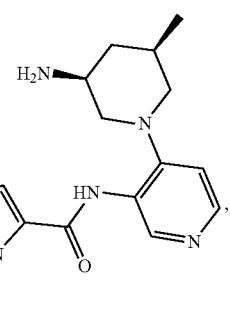

N-(4-((3S,5R)-3-amino-5-methylpiperidin-1-yl)pyridin-3-yl)-2-(2,6-difluorophenyl)thiazole-4-carboxamide or pharmaceutically acceptable salts thereof.

Another contemplated PIM kinase inhibitor is

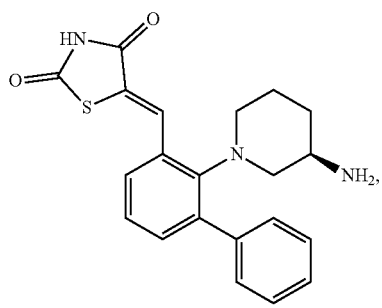

5-[[2-[(3R)-3-aminopiperidin-1-yl]biphenyl-3-yl]
methylidene]-1,3-thiazolidine-2,4-dione or a pharmaceutically acceptable salt thereof.

Accordingly, as described above, this disclosure provides for methods of treating a patient with a cancer, wherein the method includes administering a therapeutically effective amount of a compound of formula (I), (II), (III), and/or (IV) or a pharmaceutically acceptable salt thereof, and a therapeutically effective amount of a PIM kinase inhibitor, or a pharmaceutically acceptable salt thereof.

In some embodiments, the disclosure provides for methods of treating a patient with a hematological malignancy, wherein the method includes administering a therapeutically effective amount of a compound of formula (I), (II), (III), and/or (IV) or a pharmaceutically acceptable salt thereof, and a therapeutically effective amount of a PIM kinase inhibitor, or a pharmaceutically acceptable salt thereof.

In some embodiments, the methods of treatment describe administration in a patient with a hematological malignancy a therapeutically effective amount of a compound with the following structure:

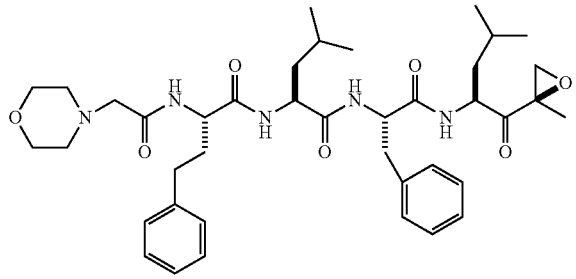 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of a PIM kinase inhibitor, or a pharmaceutically acceptable salt thereof.

In some embodiments, the PIM kinase inhibitor is selected from the following compounds: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof. In some embodiments, the PIM kinase inhibitor is a dual PIM-1/PIM-2 inhibitor, e.g., (Z)-5-(4-propoxybenzylidene)thiazolidine-2,4-dione, or a pharmaceutically acceptable salt thereof. In some embodiments, the PIM kinase inhibitor is a pan-PIM inhibitor, e.g., 5-[[2-[(3R)-3-aminopiperidin-1-yl]biphenyl-3-yl]methylidene]-1,3-thiazolidine-2,4-dione, or a pharmaceutically acceptable salt thereof.

In some embodiments, the methods of treatment describe administration in a patient with a hematological malignancy a therapeutically effective amount of a compound with the following structure:

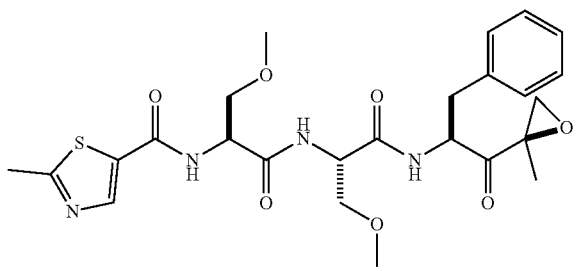 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of a PIM kinase inhibitor, or a pharmaceutically acceptable salt thereof.

In some embodiments, provided herein is a method of treating a patient with a hematological malignancy, the method including administering a therapeutically effective amount of a compound of formula (I), (II), (III), and/or (IV), or a pharmaceutically acceptable salt thereof, and a therapeutically effective amount of a PIM-2 selective kinase inhibitor, or a pharmaceutically acceptable salt thereof.

In some embodiments, the methods of treatment describe administration in a patient with a hematological malignancy a therapeutically effective amount of a compound with the following structure:

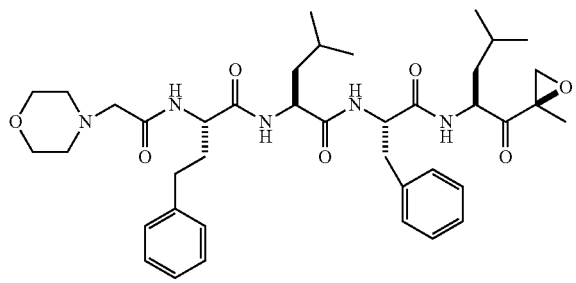 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of a PIM-2 selective kinase inhibitor, or a pharmaceutically acceptable salt thereof.

In some embodiments, the methods of treatment describe administration in a patient with a hematological malignancy a therapeutically effective amount of a compound with the following structure:

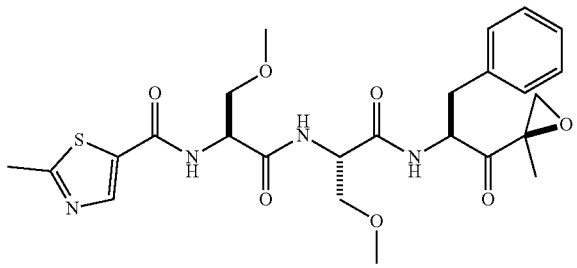 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of a PIM-2 selective kinase inhibitor, or a pharmaceutically acceptable salt thereof.

In some embodiments, a method of treatment described herein includes administration of a therapeutically effective amount of a compound of formula (I), (II), (III), and/or (IV), or a pharmaceutically acceptable salt thereof, and a therapeutically effective amount of a PIM kinase inhibitor selected from one of the following compounds: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof. In some embodiments, the PIM kinase inhibitor is a dual PIM-1/PIM-2 inhibitor, e.g., (Z)-5-(4-propoxybenzylidene)thiazolidine-2,4-dione, or a pharmaceutically acceptable salt thereof. In some embodiments, the PIM kinase inhibitor is a pan-PIM inhibitor, e.g., 5-[[2-[(3R)-3-aminopiperidin-1-yl]biphenyl-3-yl]methylidene]-1,3-thiazolidine-2,4-dione, or a pharmaceutically acceptable salt thereof.

In some embodiments, the methods of treatment describe administration in a patient with a hematological malignancy a therapeutically effective amount of a compound with the following structure:

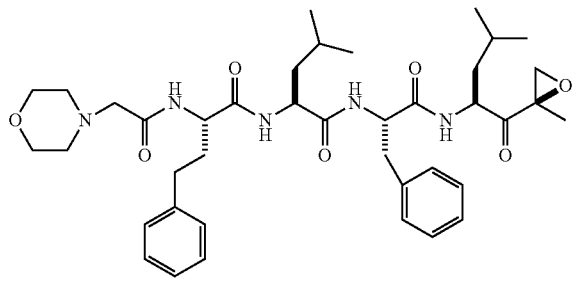 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of a PIM kinase inhibitor, that may be selected from one of the following compounds: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-

In some embodiments, the methods of treatment describe administration in a patient with a hematological malignancy a therapeutically effective amount of a compound with the following structure:

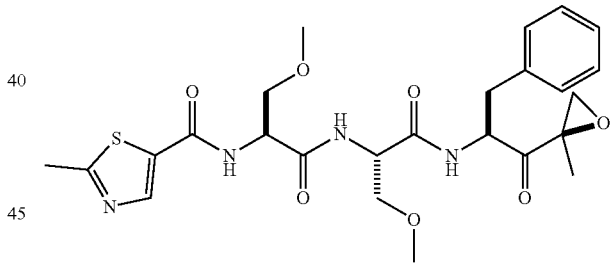

difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof. In some embodiments, the PIM kinase inhibitor is a dual PIM-1/PIM-2 inhibitor, e.g., (Z)-5-(4-propoxybenzylidene)thiazolidine-2,4-dione, or a pharmaceutically acceptable salt thereof. In some embodiments, the PIM kinase inhibitor is a pan-PIM inhibitor, e.g., 5-[[2-[(3R)-3-aminopiperidin-1-yl]biphenyl-3-yl]methylidene]-1,3-thiazolidine-2,4-dione, or a pharmaceutically acceptable salt thereof.

Provided herein is a method of treating a patient with multiple myeloma, wherein the method includes administering a therapeutically effective amount of a compound of formula (I), (II), (III), and/or (IV), or a pharmaceutically acceptable salt thereof, and a therapeutically effective amount of a PIM kinase inhibitor, or a pharmaceutically acceptable salt thereof.

In some embodiments, the methods of treatment describe administration in a patient with multiple myeloma therapeutically effective amount of a compound with the following structure:

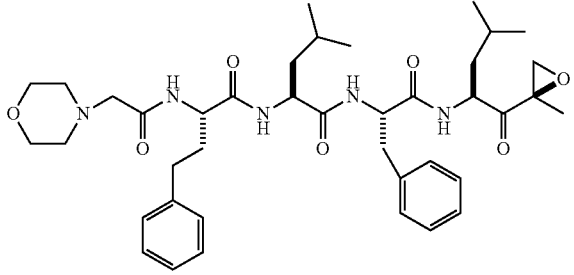

or a pharmaceutically acceptable salt thereof, and a therapeutically effective amount of PIM-2 selective kinase inhibitor, or a pharmaceutically acceptable salt thereof.

In some embodiments, the methods of treatment describe administration in a patient with multiple myeloma a therapeutically effective amount of a compound with the following structure:

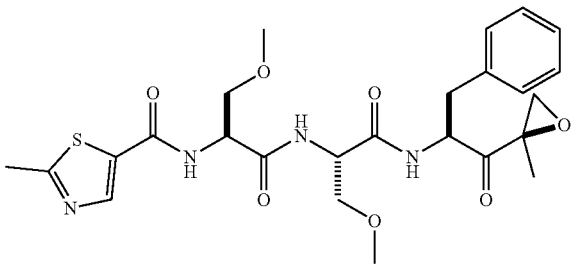 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM-2 selective kinase inhibitor, or a pharmaceutically acceptable salt thereof.

In some embodiments, the methods of treatment describe administration in a patient with multiple myeloma a therapeutically effective amount of a compound with the following structure:

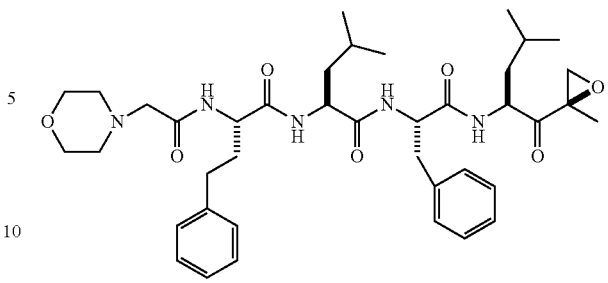

or a pharmaceutically acceptable salt thereof, and a therapeutically effective amount of a PIM kinase inhibitor, or a pharmaceutically acceptable salt thereof.

In some embodiments, the methods of treatment describe administration in a patient with multiple myeloma a therapeutically effective amount of a compound with the following structure:

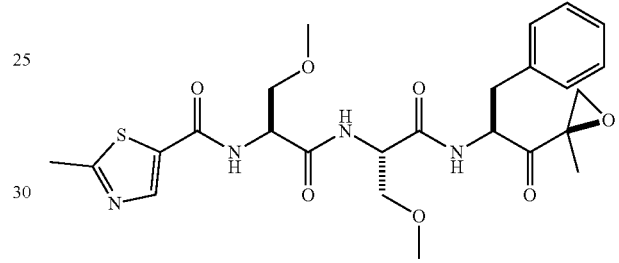

or a pharmaceutically acceptable salt thereof, an a therapeutically effective amount of a PIM kinase inhibitor, or a pharmaceutically acceptable salt thereof.

In some embodiments, provided herein is a method of treating a patient with multiple myeloma, the method including administering a therapeutically effective amount of a compound of formula (I), (II), (III), and/or (IV), or a pharmaceutically acceptable salt thereof, and a therapeutically effective amount of a PIM-2 selective kinase inhibitor, or a pharmaceutically acceptable salt thereof.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. Another example is a freeze-dried preparation that can be reconstituted prior to administration. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent in addition to a cyclodextrin and a buffer.

Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect. In general, compositions intended for parenteral use (e.g., intravenous, subcutaneous injection) include a substituted cyclodextrin. Compositions administered via other routes, particularly the oral route, include a substituted or unsubstituted cyclodextrin.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified peptide epoxyketone proteasome inhibitor in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, the peptide epoxyketone proteasome inhibitors provided herein may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Release agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A peptide epoxyketone proteasome inhibitor can be administered by aerosol. This is accomplished by preparing an aqueous aerosol, liposomal preparation, or solid particles containing the composition. A nonaqueous (e.g., fluorocarbon propellant) suspension could be used. In some embodiments, sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions suitable for parenteral administration comprise one or more peptide epoxyketone proteasome inhibitors in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), ethanol, polyols (such as glycerol, propylene glycol, polyethylene glycol, and the like), buffer (such as citrate buffer), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Prevention of the action of microorganisms may be accomplished by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

Formulation methods for peptide epoxyketone proteasome compounds include those described in applications WO 13/169282 and WO 13/169897, the contents of each is hereby incorporated by reference in its entirety.

The concentration of a disclosed compound in a pharmaceutically acceptable mixture will vary depending on several factors, including the dosage of the compound to be administered, the pharmacokinetic characteristics of the compound (s) employed, and the route of administration. In general, the compositions provided herein may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds. The dosage will be an effective amount depending on several factors including the overall health of a patient, and the formulation and route of administration of the selected compound(s).

Also provided herein is a conjoint therapy wherein one or more other therapeutic agents are administered with a peptide epoxyketone proteasome inhibitor described herein or a pharmaceutical composition comprising a peptide epoxyketone proteasome inhibitor described herein. Such conjoint treatment may be achieved by way of the simultaneous, sequential, or separate dosing of the individual components of the treatment. In certain embodiments, a peptide epoxyketone proteasome inhibitor described herein is conjointly administered with one or more other proteasome inhibitor(s). In certain embodiments, a peptide epoxyketone proteasome inhibitor described herein is conjointly administered with one or more PIM kinase inhibitors.

In certain embodiments, a peptide epoxyketone proteasome inhibitor described herein is simultaneously administered with one or more PIM kinase inhibitors.

In certain embodiments, a peptide epoxyketone proteasome inhibitor described herein is sequentially administered with one or more PIM kinase inhibitors. In certain embodiments, a peptide epoxyketone proteasome inhibitor described herein is administered before administration of one or more PIM kinase inhibitors. In certain embodiments, a peptide epoxyketone proteasome inhibitor described herein is administered after administration of one or more PIM kinase inhibitors.

In certain embodiments, a peptide epoxyketone proteasome inhibitor described herein is conjointly administered with one or more PIM kinase inhibitors that are selective for PIM-2. For example, the PIM kinase inhibitor can be selective for PIM-2 over other PIM isoforms.

In some embodiments, the ratio of a peptide epoxyketone proteasome inhibitor to a PIM kinase inhibitor administered is between about 3:1 to about 1:3 (e.g. 3:1, 2.8:1, 2.6:1, 2.5:1, 2.4:1, 2.2:1, 2:1, 1.8:1, 1.6:1, 1.5:1, 1.4:1, 1.2:1, 1:1.2, 1:1.4, 1:1.5, 1:1.6, 1:1.8, 1:2, 1:2.2, 1:2.4, 1:2.5, 1:2.6, 1:2.8, or 1:3). In some embodiments, the ratio of the peptide epoxyketone proteasome inhibitor to the PIM kinase inhibitor administered is 1:1.

EXAMPLES

Example 1—Confirmation of PIM-2 as a Proteasome Substrate Post Carfilzomib Treatment Multiple myeloma cells were used to identify pro-survival proteins that were stabilized upon carfilzomib exposure by monitoring an increase in ubiquitination at specific sites associated with degradation. Two multiple myeloma cell lines, U266 and NCI-H929, were treated for 1 and 4 hours at 125 nM concentration of carfilzomib and bortezomib. DMSO treated cells were used as a control. The concentrations of active agents used were set at the $IC_{80}$ of chymotrypsin activity inhibition and 48 hr cytotoxicity. The subunit inhibition profile obtained for these concentrations in vitro mimicked the subunit inhibition profile for carfilzomib in patients treated with a dose of 27 mg/m². Washed cell pellets were processed and profiled for ubiquitin modified proteins using a specific di-glycine antibody (PTMScan® Ubiquitin Remnant Motif (K-ε-GG) Kit #5562) that recognizes all lysine ubiquitin linkages on ubiquitin ligase substrates. All lysines on a protein that are modified with ubiquitin can be identified by this approach, and the lysines distal from the phosphorylation sites can then be associated with degradation. PIM-2 was identified as one protein demonstrating a significant increase in ubiquitination at lysine 61, distal from both phosphorylation sites on PIM-2, in both cell lines with both drugs (Table 1). The increase in ubiquitin was also time dependent in NCI-H929 (Table 1).

TABLE 1

| | Cell line (time) | | | | | |
|---|---|---|---|---|---|---|
| | U266 (4 hr) | | H929 (4 hr) | | H929 (1 hr) | |
| Compound | CFZ | BTZ | CFZ | BTZ | CFZ | BTZ |
| Ubiquitin fold increases | 34.6 | 31.5 | 24.9 | 21.4 | 10.7 | 11 |

CFZ = carfilzomib;
BTZ = bortezomib

Example 2—Knockdown of PIM-2 Synergizes with Proteasome Inhibition

Synergy of PIM-2 inhibition with a peptide epoxyketone proteasome inhibitors was explored with a PIM-2 knockdown generated using a SMARTpool of four Dharmacon siRNA in two multiple myeloma cell lines (U266 and NCI-H929).

Cells were treated with carfilzomib 24 hours post transfection, and cell viability was measured by Cell Titer Glo (Promega) 48 hours post exposure. Eighty percent knockdown efficiency was achieved in U266, and sixty percent efficiency was determined in NCI-H929 using qPCR. Control (CTL) is the scrambled siRNA used as a control for stress caused on a cell due to transfection insult and GAPDH was used as a control for specificity of knockdown. A positive result for lowering viability is determined when the test siRNA results are less viable than both the CTL and GAPDH as a single agent and in combination (for each set: left white bars, siRNA/DMSO; middle shaded bars, siRNA/$IC_{20}$ CFZ; and right solid black bars, siRNA/$IC_{30}$ CFZ).

Referring to FIG. 1, PIM-2 knockdown significantly decreased viability as a single agent in both myeloma cell lines, where the effect was more pronounced in U266 than in NCI-H929. An unpaired column T-test was performed using Graphpad to compare the GAPDH conditions with the knockdown conditions. The two ends of the horizontal markers indicate the two data columns being compared. For the statistical significance of the data represented in FIG. 1, one asterisk represents p<0.1, two asterisks represents p<0.01, and three asterisks represents p<0.001. U266 data are averages of duplicate trials and NCI-H929 data are averages of triplicate trials.

In addition to the reduced knockdown efficiency in NCI-H929, it has also been shown that U266 cells express approximately two-fold more PIM-2 than NCI-H929 cells, suggesting that U266 may be a PIM-2 addicted cancer cell type and, therefore, particularly sensitive to a functional disruption of PIM-2 (Lu, J. et al. *Blood* published Jul. 1, 2013 online ahead of print, blood-2013-01-481457). In combination with carfilzomib, PIM-2 knockdown was efficacious in both the NCI-H929 and U266 myeloma cell lines compared to the GAPDH and CTL synergy data. Further, the synergy observed was dose dependent with greater synergy observed at concentrations of carfilzomib that induced 30% death ($IC_{30}$) versus concentrations that induced 20% death ($IC_{20}$).

Example 3—Effect of Carfilzomib in Combination with (Z)-5-(4-propxybenzylidene) thazolidine-2,4-dione The effect of proteasome inhibitor carfilzomib in combination with PIM-1/PIM-2 kinase inhibitor SMI-16a ((Z)-5-(4-propxybenzylidene) thazolidine-2,4-dione) in NIH-H929 and U266 cell lines was investigated.

Cells were plated at 10,000 cells/well density in 50 µL of media in a round bottom 96-well plate overnight. Carfilzomib and the PIM-1/PIM-2 kinase inhibitor SMI-16a were serially diluted 1:1.5 in DMSO from stock solutions of 20 nM and 100 µM, respectively, for dose response. 1 µL of each dilution was added to 1 mL of media and mixed. 50 µL per well of each dose diluted in media was added to the plated cells and the culture plates were incubated for 24 hours. Proliferation was measured with Celltiter-Glo (Promega) and Luminescence was measured by Tecan Infinity M1000 Pro.

Figure 2:
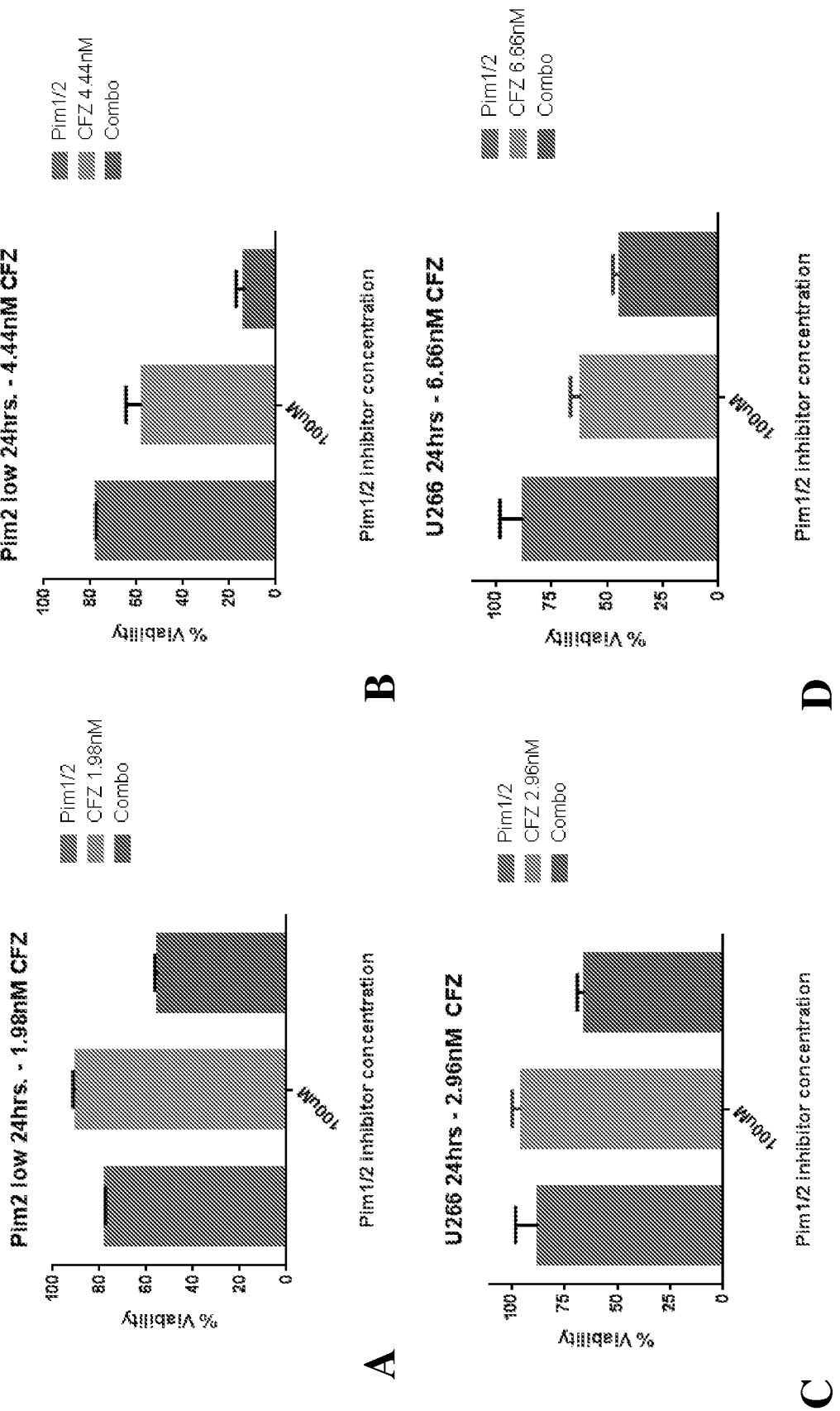
FIG. 2 is a series of graphs that show the effect of the combination of carfilzomib and the dual PIM-1/PIM-2 inhibitor (Z)-5-(4-propoxybenzylidene)thiazolidine-2,4-dione (also known as SMI-16a) on two cell lines.

Referring to FIG. 2, both NIH-H929 and U266 cell lines showed significantly lower viability after 24 hours in the presence of carfilzomib and (Z)-5-(4-propxybenzylidene) thazolidine-2,4-dione than with either (Z)-5-(4-propxybenzylidene) thazolidine-2,4-dione or carfilzomib alone.

Referring to FIG. 2A, the graph shows the percentage viability of NIH-H929 cells in the presence of 100 µM (Z)-5-(4-propxybenzylidene) thazolidine-2,4-dione alone (left bar), in the presence of 1.98 nM carfilzomib (CFZ) alone (middle bar), and with the combination of 1.98 nM carfilzomib and 100 µM (Z)-5-(4-propxybenzylidene) thazolidine-2,4-dione (right bar).

Referring to FIG. 2B, the graph shows the percentage viability of NIH-H929 cells in the presence of 100 µM (Z)-5-(4-propxybenzylidene) thazolidine-2,4-dione alone (left bar), in the presence of 4.44 nM carfilzomib (CFZ) alone (middle bar), and with the combination of 4.44 nM carfilzomib and 100 µM (Z)-5-(4-propxybenzylidene) thazolidine-2,4-dione (right bar).

Referring to FIG. 2C, the graph shows the percentage viability of U266 cells in the presence of 100 µM (Z)-5-(4-propxybenzylidene) thazolidine-2,4-dione alone (left bar), in the presence of 2.96 nM carfilzomib (CFZ) alone (middle bar), and with the combination of 2.96 nM carfilzomib and 100 µM (Z)-5-(4-propxybenzylidene) thazolidine-2,4-dione (right bar).

Referring to FIG. 2D, the graph shows the percentage viability of U266 cells in the presence of 100 µM (Z)-5-(4-propxybenzylidene) thazolidine-2,4-dione alone (left bar), in the presence of 6.66 nM carfilzomib (CFZ) alone (middle bar), and with the combination of 6.66 nM carfilzomib and 100 µM (Z)-5-(4-propxybenzylidene) thazolidine-2,4-dione (right bar).

Figure 3:
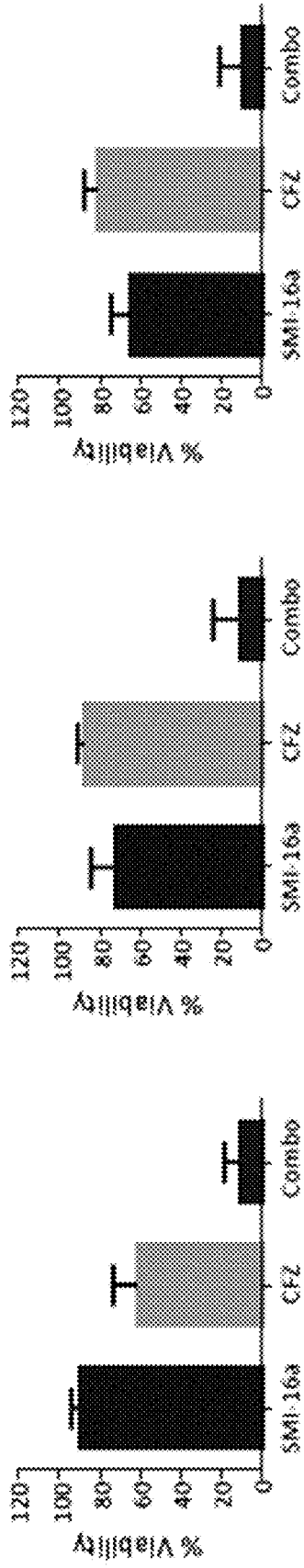
FIG. 3 is a series of graphs showing cell viability of three cancer cell lines—NIH-H929, KMS12-BM, and 8226, after 72 hours treatment with the (a) PIM-1/PIM-2 inhibitor (Z)-5-(4-propoxybenzylidene)thiazolidine-2,4-dione (also known as SMI-16a) at 10 μM alone (left bar); (b) carfilzomib at 2-4.5 nM alone (middle bar); or (c) both (right bar).
Figure 4:
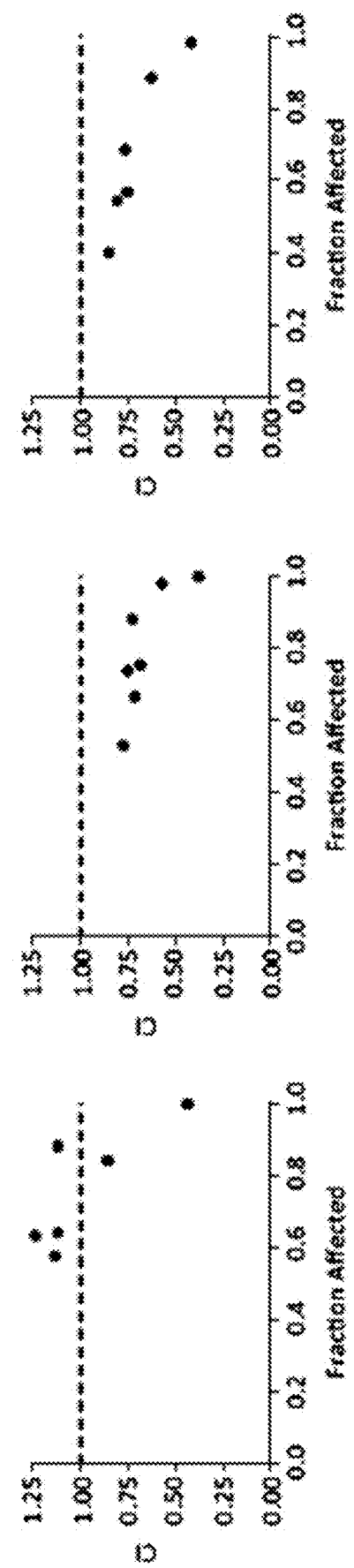
FIG. 4 shows the combination indices (CI) for synergy matrices of the data for carfilzomib and SMI-16a against cell lines NIH-H929, KMS12-BM, and 8226, calculated using Calcusyn software (Biosoft) where CI<0.90 is synergistic, 0.9<CI<1.1 is additive, and CI>1.1 is antagonistic. Against each cell line, the combination of carfilzomib and the dual PIM-1/PIM-2 inhibitor SMI-16a was synergistic.

FIG. 3 and FIG. 4 show the effect of each of carfilzomib and SMI-16a alone, or the combination of each with three different cancer cell lines NIH-H929, KMS12-BM, and 8226. As can be seen in these figures, the combination of the two therapeutics resulted in a synergistic combination (CI's less than 0.9, as shown in FIG. 4)

Example 4—Effect of Carfilzomib in Combination with Pan-PIM Inhibitor AZD-1208

The effect of proteasome inhibitor carfilzomib in combination with pan-PIM kinase inhibitor AZD-1208 (5-[[2-[(3R)-3-aminopiperidin-1-yl]biphenyl-3-yl]methylidene]-1,3-thiazolidine-2,4-dione) in NIH-H929, KMS12-BM, and 8226 cell lines was investigated.

Figure 5:
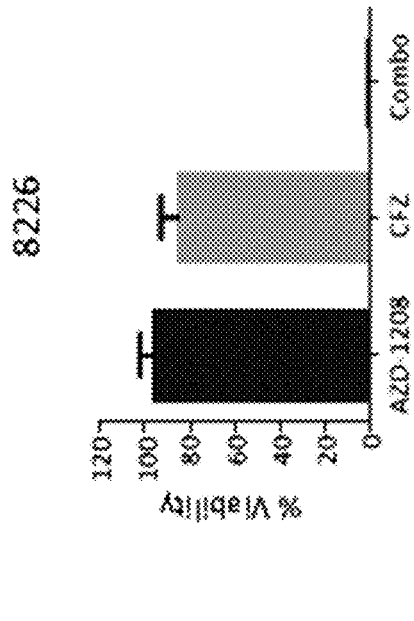
FIG. 5 is a series of graphs showing cell viability of three cancer cell lines—NIH-H929, KMS12-BM, and 8226, after 72 hours treatment with the (a) pan-PIM inhibitor 5-[[2-[(3R)-3-aminopiperidin-1-yl]biphenyl-3-yl]methylidene]-1,3-thiazolidine-2,4-dione (also known as AZD-1208) at 3-10 μM alone (left bar); (b) carfilzomib at 2-4.5 nM alone (middle bar); or (c) both (right bar).
Figure 5:
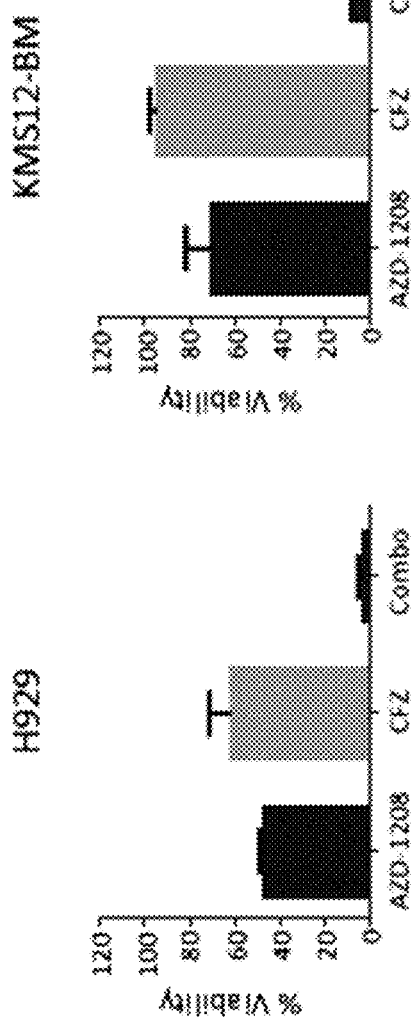
Figure 6:
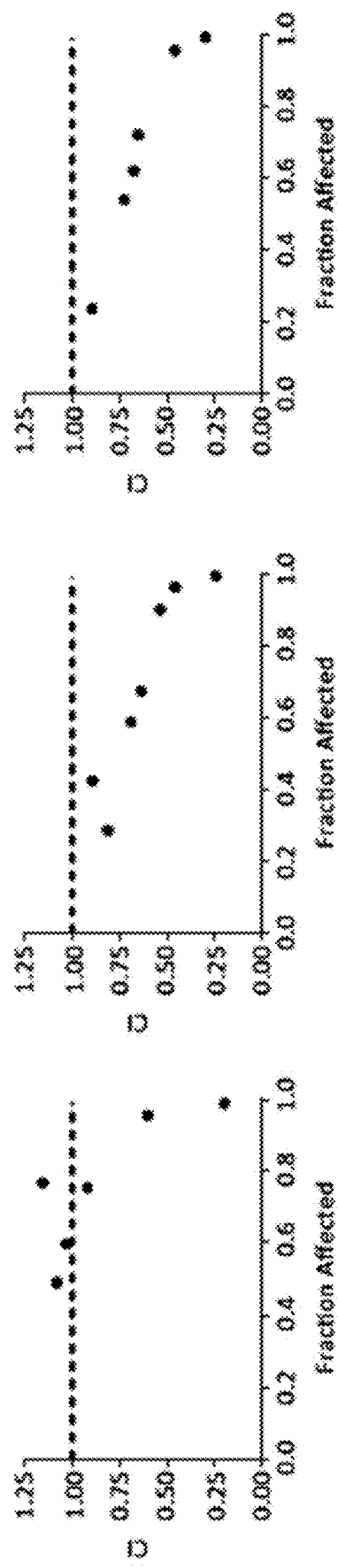
FIG. 6 shows the combination indices (CI) for synergy matrices of the data for carfilzomib and AZD-1208 against cell lines NIH-H929, KMS12-BM, and 8226, calculated using Calcusyn software (Biosoft) where CI<0.90 is synergistic, 0.9<CI<1.1 is additive, and CI>1.1 is antagonistic. Against each cell line, the combination of carfilzomib and the pan-PIM inhibitor AZD-1208 was synergistic.

Carfilzomib and the pan-PIM kinase inhibitor AZD-1208 were added to cells and incubated for 72 hours. Proliferation was measured with Celltiter-Glo (Promega). Results are shown in FIG. 5 for cells treated with 3-10 µM AZD-1208 and 2-4.5 nM carfilzomib for each of the three cell lines. The combination indices (CI) for synergy matrices results are shown in FIG. 6, wherein CI<0.9 is synergistic; 0.9<CI<1.1 are additive, and CI>1.1 are antagonistic.

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following embodiments and claims.

Specific Embodiments

1. A method for the treatment of a cancer in a patient, the method comprising administering to the patient a therapeutically effective amount of a compound of formula (I):

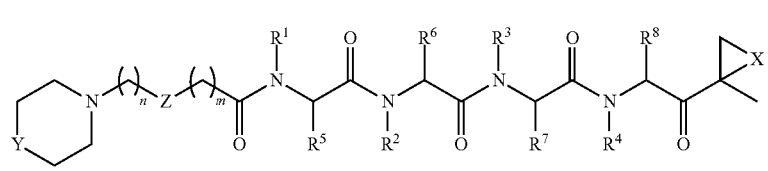

or a pharmaceutically acceptable salt thereof, wherein X is O, NH, or N-alkyl; Y is NH, N-alkyl, O, or $C(R^9)_2$;

Z is O or $C(R^9)_2$; $R^1$, $R^2$, $R^3$, and $R^4$ are all hydrogen; each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether; $R^{10}$ and $R^{11}$ are independently selected from hydrogen and $C_{1-6}$alkyl, or $R^{10}$ and $R^{11}$ together form a 3- to 6-membered carbocyclic or heterocyclic ring; $R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; m is an integer from 0 to 2; n is an integer from 0 to 2, preferably 0 or 1; and a therapeutically effective amount of a PIM kinase inhibitor, or a pharmaceutically acceptable salt thereof.

2. The method of embodiment 1, wherein X is O.

3. The method of embodiment 2, wherein $R^5$, $R^6$, $R^7$, and $R^8$ are independently selected from $C_{1-6}$alkyl, $C_{1-6}$hydroxyalkyl, and $C_{1-6}$aralkyl; and $R^9$ is hydrogen.

4. The method of embodiment 3, wherein $R^5$ and $R^7$ are independently $C_{1-6}$aralkyl and $R^6$ and $R^8$ are independently $C_{1-6}$alkyl.

5. The method of embodiment 4, wherein Y is selected from N-alkyl, O, and $CH_2$.

6. The method of embodiment 5, wherein Z is $CH_2$, and m and n are both 0.

7. The method of embodiment 5, wherein Z is $CH_2$, m is 0, and n is 2.

8. The method of embodiment 5, wherein Z is O, m is 1, and n is 2.

9. The method of embodiment 1, wherein the compound has a structure of formula (II) or a pharmaceutically acceptable salt thereof,

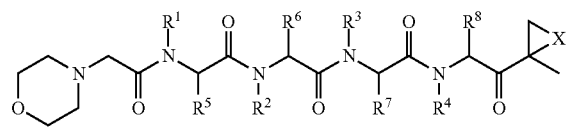

wherein X is selected from O, NH, and N-alkyl; $R^1$, $R^2$, $R^3$, and $R^4$ are all hydrogen;

$R^5$, $R^6$, $R^7$, and $R^8$ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether.

10. The method of embodiment 9, wherein X is O.

11. The method of embodiment 10, wherein $R^5$, $R^6$, $R^7$, and $R^8$ are independently selected from $C_{1-6}$alkyl, $C_{1-6}$hydroxyalkyl, and $C_{1-6}$aralkyl.

12. The method of embodiment 11, wherein $R^5$ and $R^7$ are independently $C_{1-6}$aralkyl and $R^6$ and $R^8$ are independently $C_{1-6}$alkyl.

13. The method of embodiment 1, wherein the compound has a structure of formula (III) or a pharmaceutically acceptable salt thereof,

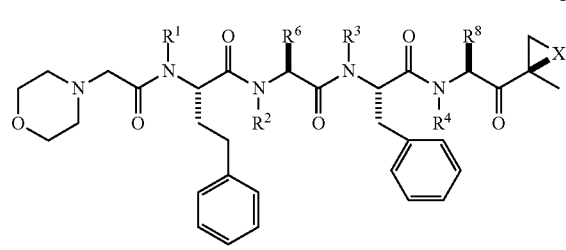

wherein X is O, NH, or N-alkyl; $R^1$, $R^2$, $R^3$, and $R^4$ are all hydrogen;

$R^6$ and $R^8$ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether.

14. The method of embodiment 13, wherein X is O.

15. The method of embodiment 14, wherein $R^6$ and $R^8$ are independently selected from $C_{1-6}$alkyl, $C_{1-6}$hydroxyalkyl, and $C_{1-6}$aralkyl.

16. The method of embodiment 15, wherein $R^6$ and $R^8$ are independently $C_{1-6}$alkyl.

17. The method of embodiment 16, wherein $R^6$ and $R^8$ are both isobutyl.

18. The method of embodiment 1, wherein the compound of formula (I) is:

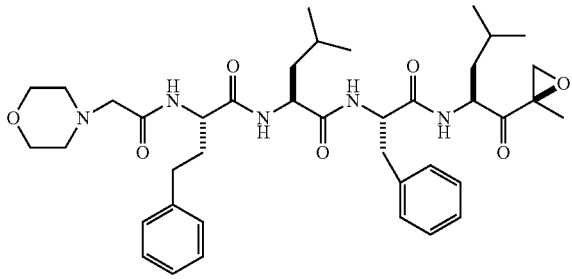 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof.

19. A method for the treatment of a cancer in a patient, the method comprising administering to the patient a therapeutically effective amount of a compound of formula (IV) or a pharmaceutically acceptable salt thereof:

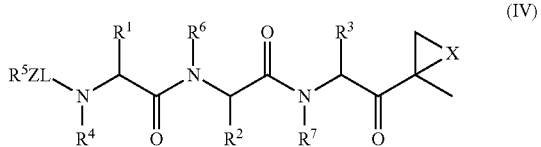

wherein L is selected from C=O, C=S, and $SO_2$; X is selected from O, S, NH, and N—$C_{1-6}$alkyl; Z is absent, $C_{1-6}$alkyl, or $C_{1-6}$alkoxy; $R^1$, $R^2$, and $R^3$ are each independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclylalkyl; $R^4$ is selected from hydrogen, $C_{1-6}$aralkyl, and $C_{1-6}$alkyl;

$R^5$ is heteroaryl; and $R^6$ and $R^7$ are independently selected from hydrogen, $C_{1-6}$alkyl, and $C_{1-6}$aralkyl, and a therapeutically effective amount of a PIM kinase inhibitor, or a pharmaceutically acceptable salt thereof.

20. The method of embodiment 19, wherein Z is absent.
21. The method of embodiment 19, wherein $R^4$, $R^6$, and $R^7$ are independently selected from hydrogen and methyl.
22. The method of embodiment 19, wherein L is C=O.
23. The method of embodiment 19, wherein L is $SO_2$.
24. The method of embodiment 19, wherein $R^1$, $R^2$, and $R^3$ are independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, $C_{1-6}$aralkyl, $C_{1-6}$heterocycloalkyl, $C_{1-6}$heteroaralkyl, and $C_{1-6}$carbocyclylalkyl.
25. The method of embodiment 24, wherein any of $R^1$, $R^2$, and $R^3$ are independently $C_{1-6}$alkyl.
26. The method of embodiment 25, wherein any of $R^1$, $R^2$, and $R^3$ are independently selected from methyl, ethyl, propyl, isopropyl, butyl, sec-butyl, and isobutyl.
27. The method of embodiment 24, wherein any of $R^1$, $R^2$, and $R^3$ are independently propargyl.
28. The method of embodiment 24, wherein any of $R^1$, $R^2$, and $R^3$ are independently $C_{1-6}$hydroxyalkyl.
29. The method of embodiment 28, wherein any of $R^1$, $R^2$, and $R^3$ are independently selected from hydroxymethyl and hydroxyethyl.
30. The method of embodiment 24, wherein any of $R^1$, $R^2$, and $R^3$ are independently $C_{1-6}$alkoxyalkyl.

31. The method of embodiment 30, wherein any of $R^1$, $R^2$, and $R^3$ are independently selected from methoxymethyl and methoxyethyl.
32. The method of embodiment 24, wherein any of $R^1$, $R^2$, and $R^3$ are independently $C_{1-6}$heteroaralkyl.
33. The method of embodiment 32, wherein any of $R^1$, $R^2$, and $R^3$ are independently selected from imidazolylmethyl, pyrazolylmethyl, and thiazolylmethyl, and pyridylmethyl.
34. The method of embodiment 24, wherein any of $R^1$, $R^2$, and $R^3$ are independently cyclohexylmethyl.
35. The method of embodiment 19, wherein $R^1$, $R^2$, and $R^3$ are all different.
36. The method of embodiment 19, wherein at least one of $R^1$ and $R^2$ is selected from $C_{1-6}$hydroxyalkyl and $C_{1-6}$alkoxyalkyl.
37. The method of embodiment 36, wherein at least one of $R^1$ and $R^2$ is $C_{1-6}$alkoxyalkyl.
38. The method of embodiment 37, wherein at least one of $R^1$ and $R^2$ is selected from methoxymethyl and methoxyethyl.
39. The method of embodiment 35, wherein $R^3$ is selected from $C_{1-6}$alkyl and $C_{1-6}$aralkyl.
40. The method of embodiment 39, wherein $R^3$ is $C_{1-6}$alkyl.
41. The method of embodiment 40, wherein $R^3$ is selected from methyl, ethyl, isopropyl, sec-butyl, and isobutyl.
42. The method of embodiment 41, wherein $R^3$ is isobutyl.
43. The method of embodiment 39, wherein $R^3$ is $C_{1-6}$aralkyl.
44. The method of embodiment 43, wherein $R^3$ is phenylmethyl.
45. The method of embodiment 19, wherein $R^5$ is 5- or 6-membered heteroaryl.
46. The method of embodiment 45, wherein $R^5$ is selected from isoxazole, isothiazole, furan, thiophene, oxazole, thiazole, pyrazole, or imidazole.
47. The method of embodiment 46, wherein $R^5$ is selected from isoxazole, furan, or thiophene.
48. The method of embodiment 47, wherein $R^5$ is furan or thiophene.
49. The method of embodiment 48, wherein $R^5$ is unsubstituted furan-3-yl or thien-2-yl.
50. The method of embodiment 47, wherein $R^5$ is isoxazol-3-yl or isoxazol-5-yl.
51. The method of embodiment 50, wherein $R^5$ is isoxazol-3-yl that has a substituent at the 5-position.
52. The method of embodiment 50, wherein $R^5$ is isoxazol-5-yl that has a substituent at the 3-position.
53. The method of embodiment 51 or 52, wherein the substituent is selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, ($C_{1-6}$alkyl)$_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl.
54. The method of embodiment 53, wherein the substituent is selected from methyl, ethyl, isopropyl, and cyclopropylmethyl.
55. The method of embodiment 53, wherein the substituent is selected from $C_{1-6}$heteroaralkyl and $C_{1-6}$heterocycloalkyl.
56. The method of embodiment 55, wherein the substituent is 1,2,4-triazol-5-ylmethyl.
57. The method of embodiment 55, wherein the substituent is azetidin-1-ylmethyl.
58. The method of embodiment 55, wherein the substituent is

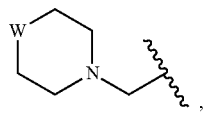

wherein W is O, NR, or CH$_2$, and R is H or C$_{1-6}$alkyl.

59. The method of embodiment 58, wherein W is O.

60. The method of embodiment 55, wherein the substituent is selected from C$_{1-6}$alkoxy and C$_{1-6}$alkoxyalkyl.

61. The method of embodiment 60, wherein the substituent is selected from methoxy, ethoxy, methoxymethyl, and methoxyethyl.

62. The method of embodiment 55, wherein the substituent is selected from carboxylic acid, aminocarboxylate, C$_{1-6}$alkylaminocarboxylate, (C$_{1-6}$alkyl)$_2$aminocarboxylate, or C$_{1-6}$alkylcarboxylate.

63. The method of embodiment 62, wherein the substituent is methyl carboxylate.

64. The method of embodiment 19, wherein the compound has the structure:

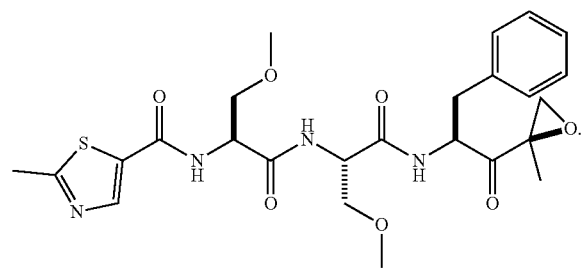 [SMILES: COC[C@H](NC(=O)c1cnc(C)s1)C(=O)N[C@@H](COC)C(=O)N[C@@H](Cc1ccccc1)C(=O)[C@@]1(C)CO1]

65. The method of embodiment 1 or 19, wherein the PIM kinase inhibitor is orally bioavailable.

66. The method of embodiment 1 or 19, wherein the PIM kinase inhibitor is selective for one or more kinases selected from the group consisting of: PIM-1, PIM-2, and PIM-3.

67. The method of embodiment 66, wherein the PIM kinase inhibitor is selective for PIM-2.

68. The method of embodiment 1 or 19, wherein the PIM kinase inhibitor is selected from the group consisting of: 7-chloro-9-ethyl-6-hydroxyisoxazolo[3,4-b]quinoline-3,4 (1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy) phenyl)imidazo[1,2-b]pyridazin-6-amine; N'-(1-(4-Chloro-2-hydroxyphenyl)propylidene)-2-((3-morpholinopropyl) amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

69. The method of embodiment 1 or 19, wherein the cancer is refractory.

70. The method of embodiment 1 or 19, wherein the cancer is resistant.

71. The method of embodiment 1 or 19, wherein the cancer is one selected from the group consisting of: bone cancer, gynecological cancer, breast cancer, hematological malignancy, skin cancer, liver cancer, kidney cancer, pancreatic cancer, brain cancer, lung cancer, and prostate cancer.

72. The method of embodiment 71, wherein the cancer is a hematological malignancy.

73. The method of embodiment 72, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

74. The method of embodiment 73, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

75. The method of embodiment 74, wherein the hematological malignancy is selected from the group consisting of: B-cell lymphoma and multiple myeloma.

76. The method of embodiment 75, wherein the hematological malignancy is multiple myeloma.

77. The method of embodiment 1 or 19, wherein the patient is one in whom PIM-2 kinase is overexpressed.

78. The method of embodiment 1 or 19, wherein the administration of the compound of formula (I) or formula (IV) and the PIM kinase inhibitor is performed concurrently.

79. The method of embodiment 1 or 19, wherein the administration of the compound of formula (I) or formula (IV) and the PIM kinase inhibitor is performed sequentially.

80. The method of embodiment 77, wherein the administration of the compound of formula (I) or formula (IV) is performed before administration of the PIM kinase inhibitor.

81. The method of embodiment 77, wherein the administration of the compound of formula (I) or formula (IV) is performed after administration of the PIM kinase inhibitor.

82. A method for the treatment of a hematological malignancy in a patient, the method comprising administering to the patient a therapeutically effective amount of a compound with the following formula:

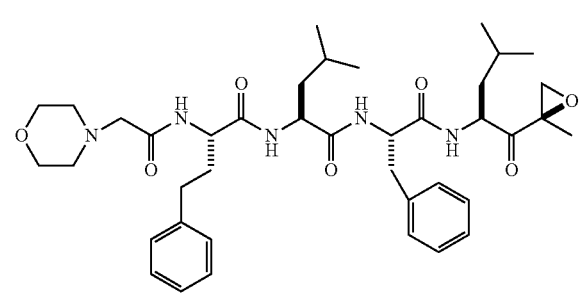 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of PIM kinase inhibitor, or a pharmaceutically acceptable salt thereof.

83. The method of embodiment 82, wherein the PIM kinase inhibitor is selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

84. The method of embodiment 82, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

85. The method of embodiment 84, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

86. The method of embodiment 85, wherein the hematological malignancy is selected from: B-cell lymphoma and multiple myeloma.

87. The method of embodiment 84, wherein the hematological malignancy is multiple myeloma.

88. A method for the treatment of a hematological malignancy in a patient, the method comprising administering to the patient a therapeutically effective amount of a compound with the following formula:

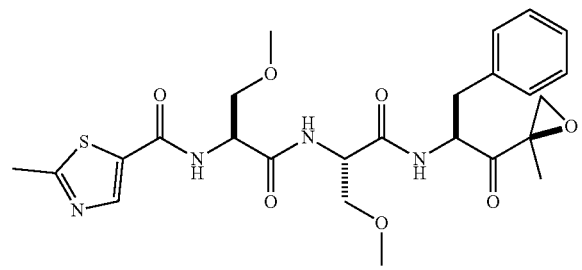 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM kinase inhibitor, or a pharmaceutically acceptable salt thereof.

89. The method of embodiment 88, wherein the PIM kinase inhibitor is selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

90. The method of embodiment 88, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

91. The method of embodiment 90, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

92. The method of embodiment 91, wherein the hematological malignancy is selected from: B-cell lymphoma and multiple myeloma.

93. The method of embodiment 92, wherein the hematological malignancy is multiple myeloma.

94. A method for the treatment of a hematological malignancy in a patient, the method comprising administering to the patient a therapeutically effective amount of a compound with the following formula:

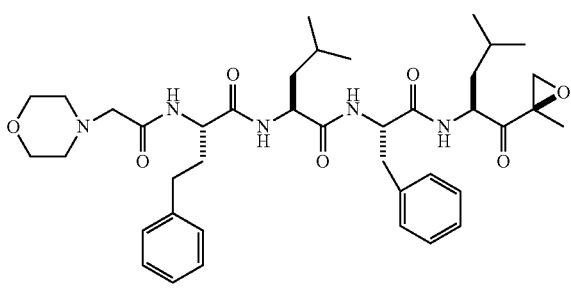 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of PIM-2 selective kinase inhibitor, or a pharmaceutically acceptable salt thereof.

95. The method of embodiment 94, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

96. The method of embodiment 95, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

97. The method of embodiment 96, wherein the hematological malignancy is selected from the group consisting of: B-cell lymphoma and multiple myeloma.

98. The method of embodiment 97, wherein the hematological malignancy is multiple myeloma.

99. A method for the treatment of a hematological malignancy in a patient, the method comprising administering to the patient a therapeutically effective amount of a compound with the following formula:

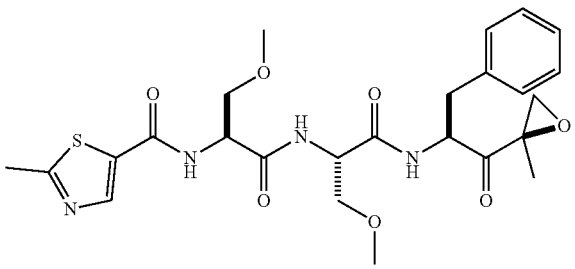 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM-2 selective kinase inhibitor, or a pharmaceutically acceptable salt thereof.

100. The method of embodiment 99, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

101. The method of embodiment 100, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

102. The method of embodiment 101, wherein the hematological malignancy is selected from: B-cell lymphoma and multiple myeloma.

103. The method of embodiment 102, wherein the hematological malignancy is multiple myeloma.

104. A method for the treatment of a hematological malignancy in a patient, the method comprising administering to the patient a therapeutically effective amount of a compound with the following formula:

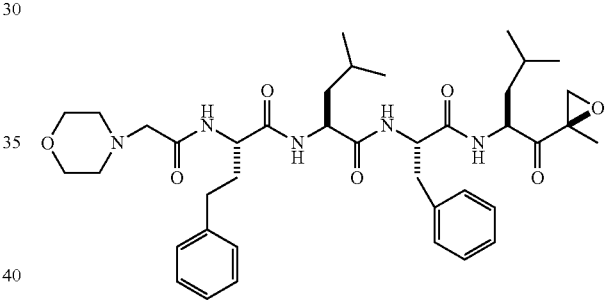

or a pharmaceutically acceptable salt thereof, and a therapeutically effective amount of PIM kinase inhibitor selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

105. The method of embodiment 104, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

106. The method of embodiment 105, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

107. The method of embodiment 106, wherein the hematological malignancy is selected from: B-cell lymphoma and multiple myeloma.

108. The method of embodiment 107, wherein the hematological malignancy is multiple myeloma.

109. A method for the treatment of a hematological malignancy in a patient, the method comprising administering to the patient a therapeutically effective amount of a compound with the following formula:

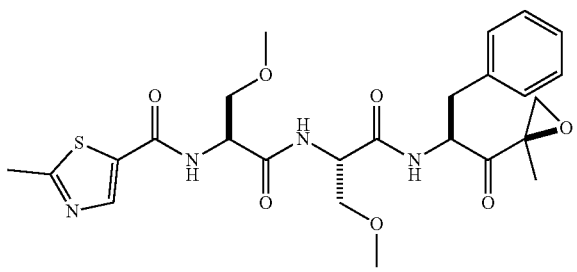 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM kinase inhibitor selected from the group consisting of: 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy)phenyl)imidazo[1,2-b]pyridazin-6-amine; N'-(1-(4-Chloro-2-hydroxyphenyl)propylidene)-2-((3-morpholinopropyl)amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

110. The method of embodiment 109, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

111. The method of embodiment 110, wherein the hematological malignancy is selected from the group consisting of: AIDS-related lymphoma, B-cell lymphoma, cutaneous T-cell lymphoma, Hodgkin lymphoma, non-Hodgkin lymphoma, mycosis fungoides, primary central nervous system lymphoma, Sézary syndrome, Waldenström macroglobulinemia, chronic myeloproliferative disorders, Langerhans cell histiocytosis, multiple myeloma, and plasma cell neoplasms.

112. The method of embodiment 111, wherein the hematological malignancy is selected from: B-cell lymphoma and multiple myeloma.

113. The method of embodiment 112, wherein the hematological malignancy is multiple myeloma.

114. A method for the treatment of multiple myeloma in a patient, the method comprising administering to the patient a therapeutically effective amount of a compound of formula (I):

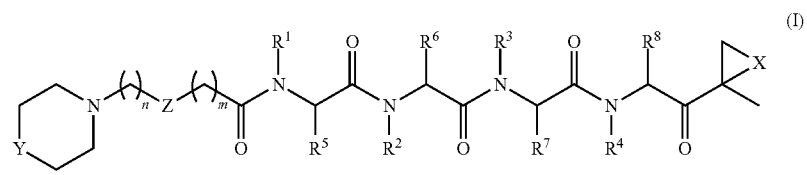

or a pharmaceutically acceptable salt thereof, wherein X is O, NH, or N-alkyl; Y is NH, N-alkyl, O, or $C(R^9)_2$; Z is O or $C(R^9)_2$; $R^1$, $R^2$, $R^3$, and $R^4$ are all hydrogen; each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether; $R^{10}$ and $R^{11}$ are independently selected from hydrogen and $C_{1-6}$alkyl, or $R^{10}$ and $R^1$ together form a 3- to 6-membered carbocyclic or heterocyclic ring; $R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; m is an integer from 0 to 2;

n is an integer from 0 to 2, preferably 0 or 1; and a therapeutically effective amount of a PIM kinase inhibitor, or a pharmaceutically acceptable salt thereof.

115. A method for the treatment of multiple myeloma in a patient, the method comprising administering to the patient a therapeutically effective amount of a compound of formula (IV) or a pharmaceutically acceptable salt thereof:

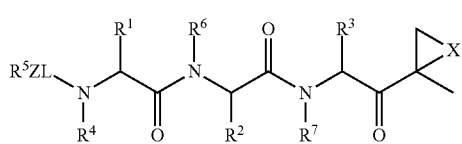

wherein L is selected from C=O, C=S, and $SO_2$; X is selected from O, S, NH, and N—$C_{1-6}$alkyl; Z is absent, $C_{1-6}$alkyl, or $C_{1-6}$alkoxy; $R^1$, $R^2$, and $R^3$ are each independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclylalkyl; $R^4$ is selected from hydrogen, $C_{1-6}$aralkyl, and $C_{1-6}$alkyl;

$R^5$ is heteroaryl; $R^6$ and $R^7$ are independently selected from hydrogen, $C_{1-6}$alkyl, and $C_{1-6}$aralkyl, and a therapeutically effective amount of a PIM kinase inhibitor, or a pharmaceutically acceptable salt thereof.

116. A method for the treatment of multiple myeloma in a patient, the method comprising administering to the patient a therapeutically effective amount of a compound with the following formula:

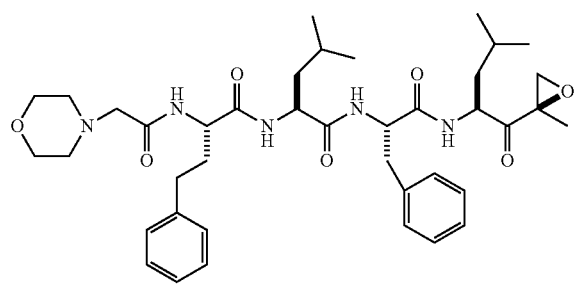 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and a therapeutically effective amount of a PIM kinase inhibitor, or a pharmaceutically acceptable salt thereof.

117. The method of embodiment 116, wherein the PIM kinase inhibitor is selected from the group consisting of: 7-chloro-9-ethyl-6-hydroxyisoxazolo[3,4-b]quinoline-3,4 (1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy) phenyl)imidazo[1,2-b]pyridazin-6-amine; N'-(1-(4-Chloro-2-hydroxyphenyl)propylidene)-2-((3-morpholinopropyl) amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

118. A method for the treatment of multiple myeloma in a patient, the method comprising administering to the patient a therapeutically effective amount of a compound with the following formula:

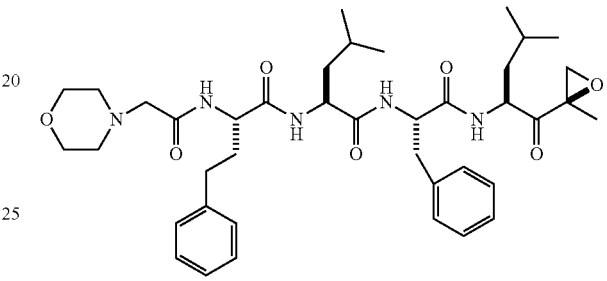

or a pharmaceutically acceptable salt thereof, and a therapeutically effective amount of PIM-2 selective kinase inhibitor, or a pharmaceutically acceptable salt thereof.

119. A method for the treatment of multiple myeloma in a patient, the method comprising administering to the patient a therapeutically effective amount of a compound with the following formula:

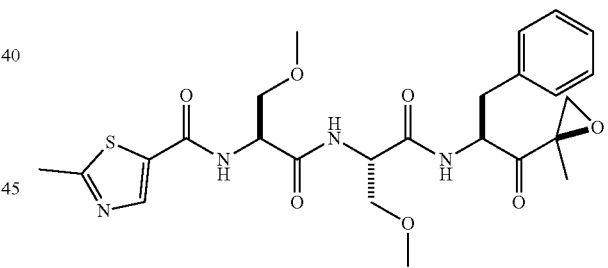

or a pharmaceutically acceptable salt thereof, and a therapeutically effective amount of PIM kinase inhibitor, or a pharmaceutically acceptable salt thereof.

120. The method of embodiment 119, wherein the PIM kinase inhibitor is selected from the group consisting of: 7-chloro-9-ethyl-6-hydroxyisoxazolo[3,4-b]quinoline-3,4 (1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N-((1-methylpiperidin-4-yl)methyl)-3-(3-(trifluoromethoxy) phenyl)imidazo[1,2-b]pyridazin-6-amine; N'-(1-(4-Chloro-2-hydroxyphenyl)propylidene)-2-((3-morpholinopropyl) amino)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-

(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophenyl)thiazole-4-carboxamide; and N-(4-((3S,5R)-3-amino-5-methylpiperidin-1-yl)pyridin-3-yl)-2-(2,6-difluorophenyl)thiazole-4-carboxamide, or a pharmaceutically acceptable salt thereof.

121. A method for the treatment of multiple myeloma in a patient, the method comprising administering to the patient a therapeutically effective amount of a compound with the following formula:

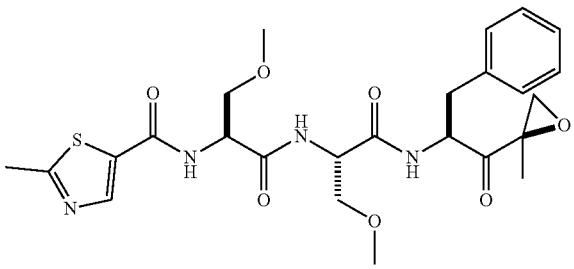 [SMILES: COC[C@H](NC(=O)c1cnc(C)s1)C(=O)N[C@@H](COC)C(=O)N[C@@H](Cc1ccccc1)C(=O)[C@@]1(C)CO1]

or a pharmaceutically acceptable salt thereof, and a therapeutically effective amount of PIM-2 selective kinase inhibitor, or a pharmaceutically acceptable salt thereof.

What is claimed:

1. A method for the treatment of a multiple myeloma in a patient, the method comprising administering to the patient
   (a) a therapeutically effective amount of a proteasome inhibitor carfilzomib having a structure of:

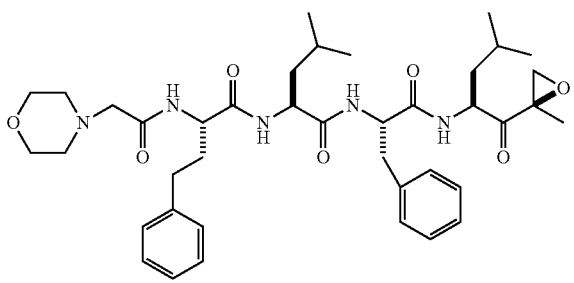 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof, and
   (b) a PIM kinase inhibitor, or a pharmaceutically acceptable salt thereof, wherein the ratio of carfilzomib to the PIM kinase inhibitor administered is between about 3:1 to about 1:3, or is 1:1, wherein the PIM kinase inhibitor comprises 5-[[2-[(3R)-3-aminopiperidin-1-yl]biphenyl-3-yl]methylidene]-1,3-thiazolidine-2,4-dione or ((Z)-5-(4-propxybenzylidene) thiazolidine-2,4-dione) or a pharmaceutically acceptable salt thereof.

2. The method of claim 1, wherein the PIM kinase inhibitor or pharmaceutically acceptable salt thereof is orally bioavailable.

3. The method of claim 1, wherein the patient is one in whom PIM-2 kinase is overexpressed.

4. The method of claim 1, wherein the proteasome inhibitor and the PIM kinase inhibitor or pharmaceutically acceptable salt thereof are administered concurrently.

5. The method of claim 1, wherein the proteasome inhibitor and the PIM kinase inhibitor or pharmaceutically acceptable salt thereof are administered sequentially.

6. The method of claim 5, wherein the proteasome inhibitor is administered prior to the PIM kinase inhibitor or pharmaceutically acceptable salt thereof.

7. The method of claim 5, wherein the proteasome inhibitor is administered after the PIM kinase inhibitor or pharmaceutically acceptable salt thereof.

8. The method of claim 1, wherein the PIM kinase inhibitor comprises 5-[[2-[(3R)-3-aminopiperidin-1-yl]biphenyl-3-yl]methylidene]-1,3-thiazolidine-2,4-dione, or a pharmaceutically acceptable salt thereof.

9. The method of claim 1, wherein the proteasome inhibitor is administered in a dose range from about 0.01 to about 50 mg/kg of body weight per day.

10. The method of claim 9, wherein the proteasome inhibitor is administered in 1-4 divided doses per day.

11. The method of claim 10, wherein the proteasome inhibitor is administered in 1 dose per day.

12. The method of claim 1, wherein the PIM kinase inhibitor or pharmaceutically acceptable salt thereof is administered in a dose range from about 0.01 to about 50 mg/kg of body weight per day.

13. The method of claim 12, wherein the PIM kinase inhibitor or pharmaceutically acceptable salt thereof is administered in 1-4 divided doses per day.

14. The method of claim 13, wherein the PIM kinase inhibitor or pharmaceutically acceptable salt thereof is administered in 1 dose per day.

15. The method of claim 1, wherein the ratio of carfilzomib to the PIM kinase inhibitor or pharmaceutically acceptable salt thereof administered is 1:1.

16. The method of claim 1, wherein the PIM kinase inhibitor comprises ((Z)-5-(4-propxybenzylidene) thazolidine-2,4-dione), or a pharmaceutically acceptable salt thereof.

* * * * *